United States Patent [19]

Yamagishi et al.

[11] Patent Number: 4,990,455

[45] Date of Patent: Feb. 5, 1991

[54] NOVEL HUMAN TNF POLYPEPTIDE MUTANTS AND DNA'S ENCODING SAID MUTANTS

[75] Inventors: Junichi Yamagishi, Nara; Hitoshi Kawashima, Osaka; Ryuji Furuta, Shiga; Hirotada Kotani, Osaka; Katuhisa Nakata, Nara, all of Japan

[73] Assignee: Dainippon Pharmaceutical Co., Ltd., Osaka, Japan

[21] Appl. No.: 64,609

[22] Filed: Jun. 22, 1987

[30] Foreign Application Priority Data

Jun. 20, 1986 [JP] Japan .................................. 61-145575

[51] Int. Cl.⁵ ...................... C12P 21/00; C12N 15/00; C07H 15/12
[52] U.S. Cl. .................................. 435/69.5; 435/69.1; 435/172.3; 435/320.1; 435/252.3; 435/252.33; 935/10; 536/27; 530/350; 530/351
[58] Field of Search ................ 435/68.7, 172.3, 253, 435/91, 94.8, 240.2, 252.3, 252.33, 69.1, 69.5; 536/27; 935/10, 38, 56, 60; 530/350, 351

[56] References Cited

U.S. PATENT DOCUMENTS

3,723,249  3/1973  Kubota et al. .
4,775,623  10/1988 Katsumata et al. .

FOREIGN PATENT DOCUMENTS

0155549   9/1985  European Pat. Off. .............. 435/68
0168214   1/1986  European Pat. Off. .............. 433/68
0205038  12/1986  European Pat. Off. .............. 435/68
WO86/02381 4/1986 PCT Int'l Appl. ................... 435/68

OTHER PUBLICATIONS

Agricultural & Biological Chemistry, 36, 1675–1684 (1972).
Journal of General and Applied Microbiology 19, pp. 339–352 (1973); 16, pp. 373–391 (1970) (Kubota).
Shirai et al., Nature, vol. 313, Feb. 28, 1985, pp. 803–806.
Yamada et al., Journal of Biotechnology, vol. 3, 1985, pp. 141–153.

*Primary Examiner*—Robin L. Teskin
*Attorney, Agent, or Firm*—Wenderoth, Lind & Ponack

[57] ABSTRACT

A human TNF polypeptide mutant having an amino acid sequence of modified human TNF polypeptide, a DNA having a base sequence encoding the above human TNF polypeptide mutant and a method of producing the above human TNF polypeptide mutant by culturing a host transformed with a vector having inserted therein the above DNA. The above human TNF polypeptide mutant is soluble and has antitumor activity.

10 Claims, 9 Drawing Sheets

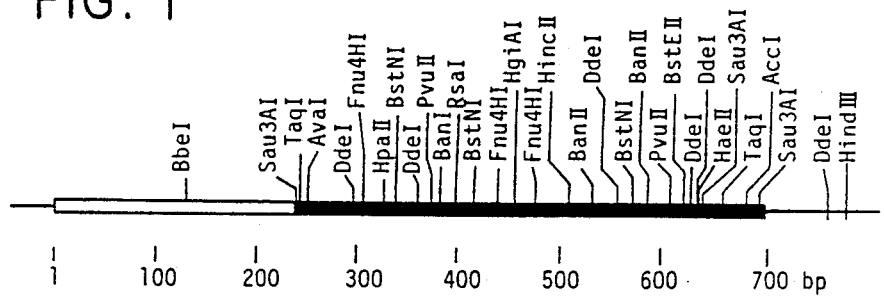
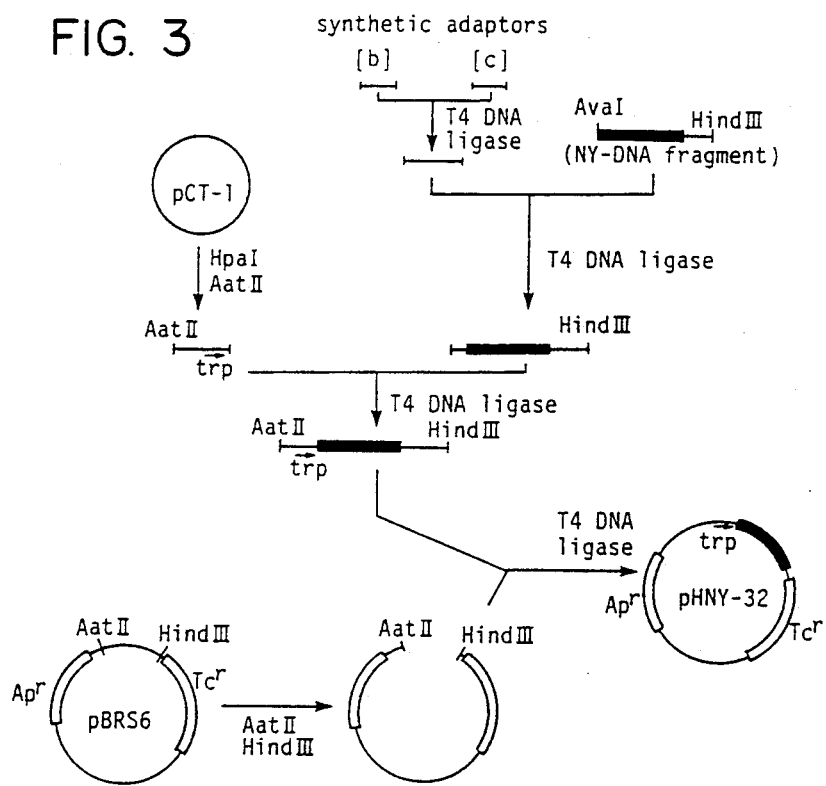

NOVEL HUMAN TNF POLYPEPTIDE MUTANTS AND DNA'S ENCODING SAID MUTANTS

This invention relates to novel human tumor necrosis factor (hereinafter referred to as TNF) polypeptide mutants, a process for production thereof, and DNAs encoding these mutants.

TNF is a physiologically active substance discovered by Carswell et al. in 1975 [Proc. Natl. Acad. Sci., USA, 72, 3666 (1975)]. It is characterized by showing strong cytotoxic activity against tumor cells in vitro and necrotizing a transplanted tumor in vivo [L. J. Old, Cancer Res., 41, 361 (1981)].

In 1984 to 1985, DNAs encoding rabbit, human and mouse TNFs were isolated [European Patent Publication No. 146026, European Patent Publication No. 155549, European Patent Publication No. 158286 and Fransen et al., Nucleic Acids Res., 13, 4417 (1985)], and the entire primary structures of their TNF polypeptides were elucidated.

Isolation of DNAs encoding TNFs, particularly DNA encoding human TNF, enabled human TNF to be produced in microorganisms by genetic engineering techniques, and various properties of human TNF were studied in greater detail. These studies led to the determination that human TNF has strong cytotoxic activity in vitro and antitumor activity in vivo [D. Pennica et al., Nature, 312, 724 (1984); T. Shirai et al., Nature, 313, 803 (1985); and M. Yamada et al., J. Biotechnology, 3, 141 (1985)].

Studies on the mutation of human TNF polypeptides have also been undertaken, and several patents have been published (PCT International Patent Publication No. WO86/02381, PCT International Patent Publication No. WO86/04606, European Patent Publication No. 168214, European Patent Publication No. 155549 which corresponds to U.S. Patent Application Ser. No. 708846, and Japanese Patent Publication No. 48632/1987). The first three patents merely refer to the mutation of human TNF polypeptide composed of 157 amino acids or give a disclosure of specific mutations. The remaining two patents disclose or refer to the mutation of human TNF polypeptide composed of 155 amino acids. The human TNF polypeptide mutants of the present invention, however, differ in amino acid sequence from the mutants specifically disclosed in these patents.

The present inventors actually mutated amino acid(s) in the amino acid sequence of human TNF polypeptide composed of 155 amino acid residues and polypeptides resulting from deletion of amino acid(s) beginning with the N-terminus of the human TNF polypeptide, and examined the properties of the resulting human TNF polypeptide mutants. This work has led to the discovery that soluble polypeptides can be obtained only when specific amino acid(s) at specific site(s) in the above polypeptides are mutated. It is an object of this invention, therefore, to provide a group of soluble human TNF polypeptide mutants.

Another object of this invention is to provide human TNF polypeptide mutants which are soluble and have TNF activity.

The present inventors have found that certain mutants in the above group have cytotoxic activity and antitumor activity in vitro and in vivo almost comparable to those of human TNF. It is still another object of the invention therefore to provide human TNF polypeptide mutants having excellent cytotoxic activity and antitumor activity in vitro and in vivo.

It has also been found that other specific mutants in the above group surprisingly show excellent antitumor activity in vivo despite their very low cytotoxic activity in vitro, and that in these mutants, pyrogenicity which is undesirable for use as pharmaceuticals is considerably reduced. It is a further object of this invention therefore to provide human TNF polypeptide mutants which show very low cytotoxic activity in vitro, but excellent antitumor activity in vivo, and have reduced de-effects. The fact that these mutants show excellent activity in vivo despite their low activity in vitro indicates that structures (active centers) essential to cytotoxic activity in vitro and antitumor activity in vivo which are typical biological activities of TNF do not always exist at the same site in TNF polypeptide molecule. This also leads to the presumption that active centers of various biological activities of TNF differ from one another.

Further objects of this invention will become apparent from the following description.

To simplify the description, the following abbreviations are used in the present specification and claims.

A: adenine
C: cytosine
G: guanine
T: thymine
Ala: alanine
Arg: arginine
Asn: asparagine
Asp: aspartic acid
Cys: cysteine
Gln: glutamine
Glu: glutamic acid
Gly: glycine
His: histidine
Ile: isoleucine
Leu: leucine
Lys: lysine
Met: methionine
Phe: phenylalanine
Pro: proline
Ser serine
Thr: threonine
Trp: tryptophan
Tyr: tyrosine
Val: valine
DNA: deoxyribonucleic acid
cDNA: complementary DNA
dATP: deoxyadenosine triphosphate
dCTP: deoxycytidine triphosphate
dGTP: deoxyguanosine triphosphate
dTTP: deoxythymidine triphosphate
kbp: kilo base pairs
bp: base pairs
SDS: sodium dodecylsulfate
MW: molecular weight:
KD: kilodaltons
SD sequence: Shine-Dalgarno sequence
Meth A sarcoma: methylcholanthrene-induced sarcoma In the present specification, the base sequence shown by a single strand is the base sequence of a sense strand, and the left end is a 5'-terminus and the right end, a 3'-terminus. In the amino acid sequence, the left end is an N-terminus, and the right end, a C-terminus.

BRIEF DESCRIPTION OF THE DRAWINGS

FIG. 1 shows the restriction endonuclease mapping of cloned cDNA encoding human TNF;

FIGS. 2 and 3 show the steps of constructing an expression plasmid pHNY-32 (in Example 1);

Figure 2:
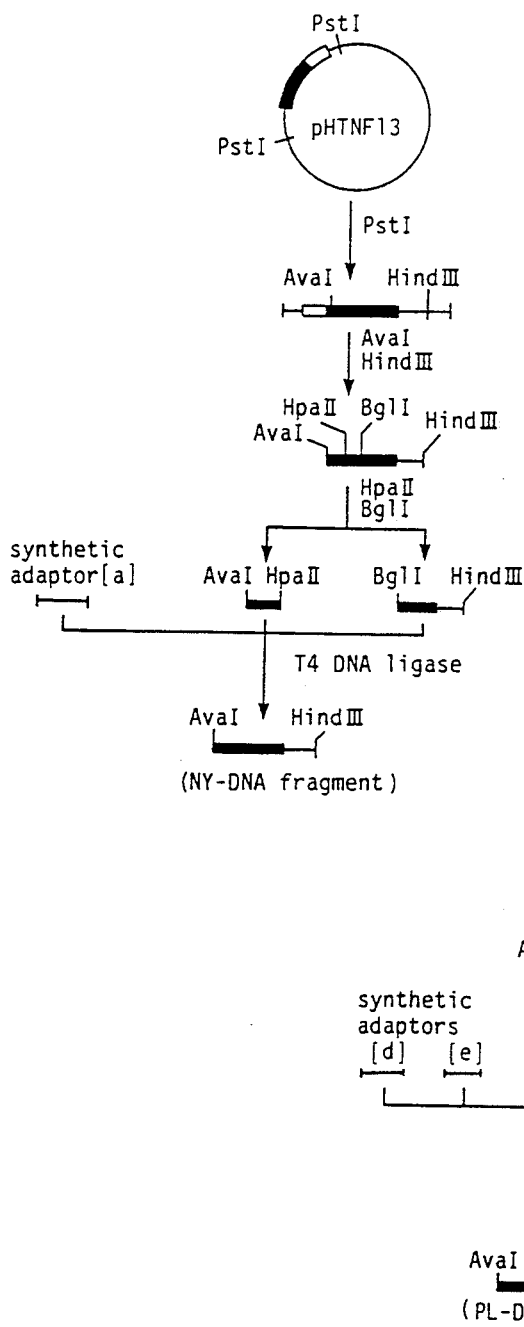

The present invention relates to a polypeptide having an amino acid sequence represented by formula [I] in Table 1 in which at least one of the 16th, 31st to 34th, 36th, 48th, 73rd, 82nd, 85th, 89th, 94th, 97th, 98th, 103rd, 113th, 115th, 117th, 118th, 131st, 132nd, 141st to 146th, and 153rd amino acid residues is replaced by another amino acid residue, with the proviso that when the 115th amino acid residue is replaced by another amino acid residue, the 67th amino acid residue and/or the 99th amino acid residue may be replaced by another amino acid residue; and a polypeptide resulting from deletion of one or at most 8 successive amino acid residues from the N-terminus of said polypeptide.

TABLE 1

| Ser | Ser | Ser | Arg | Thr | Pro | Ser | Asp | Lys | Pro |
|---|---|---|---|---|---|---|---|---|---|
| Val | Ala | His | Val | Val | Ala | Asn | Pro | Gln | Ala |
| Glu | Gly | Gln | Leu | Gln | Trp | Leu | Asn | Arg | Arg |
| Ala | Asn | Ala | Leu | Leu | Ala | Asn | Gly | Val | Glu |
| Leu | Arg | Asp | Asn | Gln | Leu | Val | Val | Pro | Ser |
| Glu | Gly | Leu | Tyr | Leu | Ile | Tyr | Ser | Gln | Val |
| Leu | Phe | Lys | Gly | Gln | Gly | Cys | Pro | Ser | Thr |
| His | Val | Leu | Leu | Thr | His | Thr | Ile | Ser | Arg |
| Ile | Ala | Val | Ser | Tyr | Gln | Thr | Lys | Val | Asn |
| Leu | Leu | Ser | Ala | Ile | Lys | Ser | Pro | Cys | Gln |
| Arg | Glu | Thr | Pro | Glu | Gly | Ala | Glu | Ala | Lys |
| Pro | Trp | Tyr | Glu | Pro | Ile | Tyr | Leu | Gly | Gly |
| Val | Phe | Gln | Leu | Glu | Lys | Gly | Asp | Arg | Leu |
| Ser | Ala | Glu | Ile | Asn | Arg | Pro | Asp | Tyr | Leu |
| Asp | Phe | Ala | Glu | Ser | Gly | Gln | Val | Tyr | Phe |
| Gly | Ile | Ile | Ala | Leu |  |  |  |  | [I] |

More specifically, the human TNF polypeptide mutants of this invention are illustrated in the following (A), (B) and (C).

(A) The human TNF polypeptide mutants which are characterized in that at least one of the following amino acid replacements is effected in the amino acid sequence of human TNF represented by formula [I]:
Replacement of
16th Ala by Val,
31st Ala by Thr,
32nd Asn by Ala, Cys, Asp, His, Ile, Arg, Ser, Thr, Val or Tyr
34th Leu by Ile,
36th Ala by Val,
48th Val by Met,
73rd Leu by Pro,
82nd Ala by Asp,
85th Tyr by His,
89th Val by Ile,
94th Ala by Thr,
97th Ser by Asn,
98th Pro by His or Leu,
103rd Thr by Pro,
113th Tyr by Cys,
115th Pro by Leu, His, Gln, Ser, Ala, Phe, Asn, Gly, Tyr, Val, Glu, Met, Ile, Asp, Trp, Lys, Arg, or Thr,
117th Tyr by His,
118th Leu by Gln,
131st Ser by Ile,
132nd Ala by Thr,
141st Asp by Tyr,
143rd Ala by Val,
144th Glu by Lys,
145th Ser by Cys,
146th Gly by Glu, and
153rd Ile by Leu.

(B) The human TNF polypeptide mutants which are characterized in that in the amino acid sequence of human TNF of formula [I] 67th Cys and/or 99th Cys is replaced by Ser and that 115th Pro is replaced by an amino acid other than Pro.

(C) The human TNF polypeptide mutants (A) or (B) in which one or at most 8 successive amino acid residues from their N-terminus are deleted.

In the above group of mutants, examples of those mutants which show excellent cytotoxic activity in vitro and antitumor activity in vivo are shown below.

Polypeptide mutants having the amino acid sequence represented by formula [I] in which
16th Ala is replaced by Val,
36th Ala is replaced by Val,
73rd Leu is replaced by Pro,
98th Pro is replaced by His or Leu,
103rd Thr is replaced by Pro,
115th Pro is replaced by His or Gln,
131st Ser is replaced by Ile, or
143rd Ala is replaced by Val.

In the above group of mutants, examples of those mutants which have low cytotoxic activity in vitro but excellent antitumor activity in vivo are shown below.

Polypeptide mutants having the amino acid sequence represented by formula [I] in which
31st Ala is replaced by Thr,
32nd Asn is replaced by Ala, Cys, Asp, His, Ile, Arg, Ser, Thr, Val or Tyr,
115th Pro is replaced by Ser, Ala, Phe, Asn, Thr, Gly, Tyr, Val, Glu, Met, Ile, Asp, Trp, Leu or Lys, or
117th Tyr is replaced by His.

Especially preferred mutants are polypeptides having the amino acid sequence of formula I) in which
32nd Asn is replaced by Tyr, His, Asp or Ser,
115th Pro is replaced by Leu, Ser, Asp or Gly, or
117th Tyr is replaced by His.

The present invention also relates to DNAs encoding the above polypeptide mutants of this invention. The DNAs of the invention will be described below with reference to formula (A) in Table 2.

TABLE 2

| (5') | TCA | TCT | TCT | CGA | ACC | CCG | AGT | GAC | AAG |
|------|-----|-----|-----|-----|-----|-----|-----|-----|-----|
| CCT | GTA | GCC | CAT | GTT | GTA | GCA | AAC | CCT | CAA |
| GCT | GAG | GGG | CAG | CTC | CAG | TGG | CTG | AAC | CGC |
| CGG | GCC | AAT | GCC | CTC | CTG | GCC | AAT | GGC | GTG |
| GAG | CTG | AGA | GAT | AAC | CAG | CTG | GTG | GTG | CCA |
| TCA | GAG | GGC | CTG | TAC | CTC | ATC | TAC | TCC | CAG |
| GTC | CTC | TTC | AAG | GGC | CAA | GGC | TGC | CCC | TCC |
| ACC | CAT | GTG | CTC | CTC | ACC | CAC | ACC | ATC | AGC |
| CGC | ATC | GCC | GTC | TCC | TAC | CAG | ACC | AAG | GTC |
| AAC | CTC | CTC | TCT | GCC | ATC | AAG | AGC | CCC | TGC |
| CAG | AGG | GAG | ACC | CCA | GAG | GGG | GCT | GAG | GCC |
| AAG | CCC | TGG | TAT | GAG | CCC | ATC | TAT | CTG | GGA |
| GGG | GTC | TTC | CAG | CTG | GAG | AAG | GGT | GAC | CGA |
| CTC | AGC | GCT | GAG | ATC | AAT | CGG | CCC | GAC | TAT |
| CTC | GAC | TTT | GCC | GAG | TCT | GGG | CAG | GTC | TAC |
| TTT | GGG | ATC | ATT | GCC | CTG- | (3') | | | [A] |

Specific examples of the DNA of this invention are the following (a), (b), (c) and (d).

(a) DNAs having a base sequence represented by formula [A] in Table 2 in which

16th codon GCA for Ala is replaced by codon GTA for Val,

31st codon GCC for Ala is replaced by codon ACC for Thr,

32nd codon AAT for Asn is replaced by codon GCT for Ala,

32nd codon AAT for Asn is replaced by codon TGC for Cys,

32nd codon AAT for Asn ;s replaced by codon GAT for Asp,

32nd codon AAT for Asn is replaced by codon CAC for His,

32nd codon AAT for Asn is replaced by codon ATC for Ile,

32nd codon AAT for Asn is replaced by codon CGA for Arg,

32nd codon AAT for Asn is replaced by codon AGC for Ser,

32nd codon AAT for Asn is replaced by codon ACT for Thr,

32nd codon AAT for Asn is replaced by codon GTC for Val,

32nd codon AAT for Asn is replaced by codon TAT for Tyr,

34th codon CTC for Leu is replaced by codon ATC for Ile,

36th codon GCC for Ala is replaced by codon GTC for Val,

48th codon GTG for Val is replaced by codon ATG for Met,

73rd codon CTC for Leu is replaced by codon CCC for Pro,

82nd codon GCC for Ala is replaced by codon GAC for Asp,

85th codon TAC for Tyr is replaced by codon CAC for His,

89th codon GTC for Val is replaced by codon ATC for Ile,

94th codon GCC for Ala is replaced by codon ACC for Thr,

97th codon AGC for Ser is replaced by codon AAC for Asn,

98th codon CCC for Pro is replaced by codon CAC for His,

98th codon CCC for Pro is replaced by codon CTC for Leu,

103rd codon ACC for Thr is replaced by codon CCC for Pro,

113th codon TAT for Tyr is replaced by codon TGT for Cys,

115th codon CCC for Pro is replaced by codon CAC for His,

115th codon CCC for Pro is replaced by codon CAG for Gln,

115th codon CCC for Pro is replaced by codon TCC for Ser,

115th codon CCC for Pro is replaced by codon GCC for Ala,

115th codon CCC for Pro is replaced by codon TTC for Phe,

115th codon CCC for Pro is replaced by codon AAC for Asn,

115th codon CCC for Pro is replaced by codon ACC for Thr,

115th codon CCC for Pro is replaced by codon GGC for Gly,

115th codon CCC for Pro is replaced by codon TAC for Tyr,

115th codon CCC for Pro is replaced by codon GTC for Val,

115th codon CCC for Pro is replaced by codon GAG for Glu,

115th codon CCC for Pro is replaced by codon ATG for Met,

115th codon CCC for Pro is replaced by codon ATC for Ile,

115th codon CCC for Pro is replaced by codon GAC for Asp,

115th codon CCC for Pro is replaced by codon TGG for Trp,

115th codon CCC for Pro is replaced by codon CTC for Leu,

115th codon CCC for Pro is replaced by codon AAG for Lys,

115th codon CCC for Pro is replaced by codon CGC for Arg,

117th codon TAT for Tyr is replaced by codon CAT for His,

118th codon CTG for Leu is replaced by codon CAG for Gln,

131st codon AGC for Ser is replaced by codon ATC for Ile,

132nd codon GCT for Ala is replaced by codon ACT for Thr,

141st codon GAC for Asp is replaced by codon TAC for Tyr,

143rd codon GCC for Ala is replaced by codon GTC for Val,

144th codon GAG for Glu is replaced by codon AAG for Lys,

145th codon TCT for Ser is replaced by codon TGT for Cys,

146th codon GGG for Gly is replaced by codon GAG for Glu, or

153rd codon ATT for Ile is replaced by codon CTG for Leu.

(b) DNAs having the base sequence of formula [A] in which codon GGC encoding 67th Cys and/or 99th Cys is replaced by codon TCT encoding Ser and that codon CCC encoding 115th Pro is replaced by a codon encoding the other amino acid mentioned above.

(c) DNAs resulting from deletion of one or at most 8 successive codons from the 5'-terminus of the above DNAs.

(d) DNAs above in which a translation initiation codon ATG is joined to the 5'-terminus, and/or a termination codon is joined to the 3'-terminus.

The DNAs encoding the novel human TNF polypeptide mutants of the invention can be produced by preparing DNA encoding human TNF or its precursor by a known method, such as the method described in European Patent Publication No. 155549 or a method of chemical synthesis, and then preparing DNAs encoding the above mutants by point mutation of the resulting DNA in accordance with the method of Wang et al [Science, 224, 1431 (1984)], or preparing DNAs encoding the above mutants by partial replacement of the resulting DNA using suitable restriction endonucleases and synthetic oligodeoxyribonucleotide adapters in which the base sequence at the desired site(s) is artificially altered.

For example, DNA encoding a polypeptide mutant. of formula [I] in which the 115th amino acid (Pro) is replaced by Leu can be produced by the following procedure.

DNA having a base sequence encoding human TNF precursor is isolated by the method described in European Patent Publication No. 155549. The base sequence of DNA encoding the human TNF precursor is shown in Table 8 hereinbelow, and a sequence from the 235th base to the 699th base in this base sequence corresponds to a base sequence encoding human TNF The codon encoding the 115th amino acid (Pro) in the amino acid sequence of human TNF corresponds to the 577th to 579th bases (CCC) in Table 8. A DNA fragment containing this codon is cut out with a combination of suitable restriction endonucleases. Separately, a DNA fragment containing a base sequence resulting from replacing the codon (CCC) for Pro in the above DNA fragment by codon (CTC) for Leu is chemically synthesized. By substituting the synthesized DNA fragment for the cut out DNA fragment, DNA encoding the above polypeptide mutant can be produced.

More specifically, a DNA fragment corresponding to the 555th to 603rd bases in Table 8 is cut out by using restriction endonucleases DdeI and PvuII, for example.

On the other hand, the oligodeoxyribonucleotide adapters having the following base sequences are chemically synthesized.

```
5'-TGAGGCCAAGCCCTGGTATGAGCTCAT-3'
3'-CCGGTTCGGGACCATACTCGA-5'
``` and

```
5'-CTATCTGGGAGGGGTCTTCCAG-3'
3'-GTAGATAGACCCTCCCCAGAAGGTC-5'
```

The resulting DNA adapters are substituted for the cut out DNA fragment corresponding to the 555th to 603rd bases in Table 8.

By inserting the DNA into a suitable expression vector so that it has a suitable sequence, introducing the vector into a suitable host, and culturing the resulting transformant by techniques known in the art, human TNF polypeptide mutants of the invention can be produced. More specifically, an expression vector for production of the polypeptide mutant of the invention can be produced by preparing a DNA fragment having a translation initiation codon ATG at the 5'-terminus and a termination codon at the 3'-terminus in the DNA having a base sequence encoding the polypeptide mutant itself of the invention, joining the DNA fragment following a suitable promoter and the SD sequence, and then inserting the resulting fragment into a vector. Examples of the promoter are lac, trp, tac, phoS, phoA, PL, and SV40 early promoter. Examples of the vector are plasmids (e.g., pBR322), phages (e.g., lambda phage derivatives), and viruses (e.g., SV40). Transformant can be obtained by introducing the resulting expression vector for production of the polypeptide mutant of the invention into a suitable host, for example, E. coli, by the method of Cohen et al. [Proc. Natl Acad. Sci., USA, 69, 2110 (1972)]. Then, by culturing the transformant under suitable culturing conditions, the desired polypeptide mutant or one in which Met is joined to its N-terminus can be produced. The cultured cells are treated of, for example, lysozyme digestion, freeze-thawing, ultrasonic rupture, or by using a French press, and then centrifuged or filtered to obtain an extract containing the polypeptide mutant of the invention. The desired polypeptide mutant can be isolated by purifying the extract in accordance with a general method of purifying proteins (such as ultra-filtration, dialysis, ion exchange chromatography, gel filtration, electrophoresis and affinity chromatography).

The reaction of an organic or inorganic acid or a base with the polypeptide mutant of the invention can give its salt.

Human TNF polypeptide mutants of the invention will be described below in more detail with reference to experimental examples.

(1) Various human TNF polypeptide mutants were produced by culturing the transformants obtained in Examples and Referential Examples given hereinbelow.

Specifically, the transformants were cultured by the method shown in Example 1-(2), and the various human TNF polypeptide mutants produced in the E. coli cells were extracted into 50 mM Tris-HCl buffer (pH 8) containing 0.1% lysozyme and 30 mM NaCl.

The amounts of the desired human TNF polypeptide mutants recovered in the extracts were measured by EIA (enzyme immunoassay) as the amount of the polypeptide which reacted immunologically with an anti-human TNF antibody. The method of determination of the human TNF polypetide mutant according to EIA is based on the following principle.

A competitive binding reaction for an anti-human TNF rabbit antiserum was done between the human TNF polypeptide mutant in an assay sample and human TNF labelled with beta-galactosidase. Then, by adding anti-rabbit IgG goat antiserum insolubilized by binding to a bacterial cell wall, a complex of enzyme-labelled human TNF/anti-human TNF rabbit antibody/anti-rabbit IgG goat antibody was formed. The reaction mixture was centrifuged to obtain a solid phase The amount of the enzyme-labelled human TNF in the above complex which was recovered in the solid phase was determined by using its enzyme activity as an index.

Specifically, 2-nitrophenyl-beta-D-galactopyranoside was used as an enzyme substrate, and the amount of the digested product (2-nitrophenol) of the substrate formed by the enzyme reaction was determined by the absorbance at a wavelength of 410 nm. The amount of the enzyme-labelled human TNF in the complex reflects the amount of the human TNF polypeptide mutant in the assay sample.

The amount of the human TNF polypeptide mutant in the assay sample was determined by using a standard curve prepared separately by using human TNF.

In the preparation of the anti-human TNF rabbit antiserum, pure human TNF produced by the method of Yamada et al. [J. Biotechnology, 3, 141 (1985)] was used as an antigen.

The results are shown in Table 3.

When the amount of the desired human TNF polypeptide mutant detected in the cell extract is nearly comparable to that of human TNF used as a control, the solubility of the polypeptide mutant is expressed as (++). Its solubility is expressed as (+) when its detected amount is smaller than the control, and as (−) when it is much smaller than the control or the desired polypeptide mutant is not detected.

It is presumed that the polypeptide mutants having solubilities expressed as (−) underwent structural change and thus markedly decreased in solubility, or were unstable in the E. coli cells.

TABLE 3

Solubilities of Human TNF Polypeptide Mutants:

| Polypeptide mutant | Mutation: position | | solubility |
|---|---|---|---|
| TNF-12T | 12th | Ala → Thr | (−) |
| TNF-13Y | 13th | His → Tyr | (−) |
| TNF-14A | 14th | Val → Ala | (−) |
| TNF-16V | 16th | Ala → Val | (++) |
| TNF-17T | 17th | Asn → Thr | (+) |
| TNF-24F | 24th | Leu → Phe | (+) |
| TNF-26R | 26th | Trp → Arg | (−) |
| TNF-31T | 31st | Ala → Thr | (++) |
| TNF-32A | 32nd | Asn → Ala | (++) |
| TNF-32C | 32nd | Asn → Cys | (++) |
| TNF-32D | 32nd | Asn → Asp | (++) |
| TNF-32H | 32nd | Asn → His | (++) |
| TNF-32I | 32nd | Asn → Ile | (++) |
| TNF-32R | 32nd | Asn → Arg | (++) |
| TNF-32S | 32nd | Asn → Ser | (++) |
| TNF-32T | 32nd | Asn → Thr | (++) |
| TNF-32V | 32nd | Asn → Val | (++) |
| TNF-32Y | 32nd | Asn → Tyr | (++) |
| TNF-32G | 32nd | Asn → Gly | (++) |
| TNF-32L | 32nd | Asn → Leu | (++) |
| TNF-34I | 34th | Leu → Ile | (++) |
| TNF-35P | 35th | Leu → Pro | (−) |
| TNF-36V | 36th | Ala → Val | (++) |
| TNF-44D | 44th | Asn → Asp | (−) |
| TNF-45P | 45th | Gln → Pro | (−) |
| TNF-48M | 48th | Val → Met | (++) |
| TNF-50P | 50th | Ser → Pro | (−) |
| TNF-54C | 54th | Tyr → Cys | (−) |
| TNF-54H | 54th | Tyr → His | (−) |
| TNF-58P | 58th | Ser → Pro | (−) |
| TNF-59L | 59th | Gln → Leu | (−) |
| TNF-60D | 60th | Val → Asp | (−) |
| TNF-60G | 60th | Val → Gly | (−) |
| TNF-62S | 62nd | Phe → Ser | (−) |
| TNF-67S | 67th | Cys → Ser | (++) |
| TNF-70Y | 70th | Thr → Tyr | (++) |
| TNF-73P | 73rd | Leu → Pro | (++) |
| TNF-82D | 82nd | Ala → Asp | (++) |
| TNF-85H | 85th | Tyr → His | (++) |

TABLE 3-continued

Solubilities of Human TNF Polypeptide Mutants:

| Polypeptide mutant | Mutation: position | | solubility |
|---|---|---|---|
| TNF-89I | 89th | Val → Ile | (++) |
| TNF-93P | 93rd | Ser → Pro | (−) |
| TNF-94T | 94th | Ala → Thr | (++) |
| TNF-97N | 97th | Ser → Asn | (++) |
| TNF-98H | 98th | Pro → His | (++) |
| TNF-98L | 98th | Pro → Leu | (++) |
| TNF-99S | 99th | Cys → Ser | (++) |
| TNF-103P | 103rd | Thr → Pro | (++) |
| TNF-113C | 113th | Tyr → Cys | (++) |
| TNF-115H | 115th | Pro → His | (++) |
| TNF-115Q | 115th | Pro → Gln | (++) |
| TNF-115S | 115th | Pro → Ser | (++) |
| TNF-115A | 115th | Pro → Ala | (++) |
| TNF-115F | 115th | Pro → Phe | (+) |
| TNF-115N | 115th | Pro → Asn | (++) |
| TNF-115T | 115th | Pro → Thr | (++) |
| TNF-115G | 115th | Pro → Gly | (++) |
| TNF-115Y | 115th | Pro → Tyr | (++) |
| TNF-115V | 115th | Pro → Val | (++) |
| TNF-115E | 115th | Pro → Glu | (++) |
| TNF-115M | 115th | Pro → Met | (+) |
| TNF-115I | 115th | Pro → Ile | (++) |
| TNF-115D | 115th | Pro → Asp | (++) |
| TNF-115W | 115th | Pro → Trp | (++) |
| TNF-115L | 115th | Pro → Leu | (++) |
| TNF-115K | 115th | Pro → Lys | (++) |
| TNF-115R | 115th | Pro → Arg | (+) |
| TNF-117H | 117th | Tyr → His | (++) |
| TNF-118Q | 118th | Leu → Gln | (++) |
| TNF-121G | 121st | Val → Gly | (−) |
| TNF-124Q | 124th | Leu → Gln | (−) |
| TNF-128A | 128th | Asp → Ala | (−) |
| TNF-128N | 128th | Asp → Asn | (−) |
| TNF-131I | 131st | Ser → Ile | (++) |
| TNF-132T | 132nd | Ala → Thr | (++) |
| TNF-135D | 135th | Asn → Asp | (+) |
| TNF-138Y | 138th | Asp → Tyr | (+) |
| TNF-141Y | 141st | Asp → Tyr | (++) |
| TNF-143V | 143rd | Ala → Val | (++) |
| TNF-144K | 144th | Glu → Lys | (++) |
| TNF-145C | 145th | Ser → Cys | (++) |
| TNF-146E | 146th | Gly → Glu | (++) |
| TNF-148D | 148th | Val → Asp | (−) |
| TNF-148G | 148th | Val → Gly | (−) |
| TNF-150L | 150th | Phe → Leu | (−) |
| TNF-151E | 151st | Gly → Glu | (−) |
| TNF-153L | 153rd | Ile → Leu | (++) |
| TNF-115L-Ser67 | | | (++) |
| TNF-115LΔN8-Ser67 | | | (++) |
| TNF-115LΔN8 | | | (++) |

(2) Table 4 shows the isoelectric points and cytotoxic activities of human TNF (as a control) and the various human TNF polypeptide mutants of the invention obtained in Examples given hereinbelow.

The cytotoxic activity was evaluated on mouse L-M cells (ATCC, CCL 1.2) by the method of Yamada et al. [J. Biotechnology, 3, 141 (1985)].

The human TNF polypeptide mutants which were determined to be homogeneous from SDS-polyacrylamide gel electrophoretic analysis [U. K. Laemmli, Nature (London), 227, 680 (1970)] were used in this test.

TABLE 4

Properties of Human TNF Polypeptide Mutant: Isoelectric point and cytotoxoc activity

| Mutant polypeptide | Isoelectric point (pI) | Cytotoxic activity (U/μg) |
|---|---|---|
| Human TNF | 5.9 | 2,080 |
| TNF-16V | 5.7 | 310 |
| TNF-31T | 5.8 | 12 |
| TNF-32Y | 5.9 | 0.18 |
| TNF-32H | 6.1 | 32 |

TABLE 4-continued

Properties of Human TNF Polypeptide Mutant: Isoelectric point and cytotoxoc activity

| Mutant polypeptide | Isoelectric point (pI) | Cytotoxic activity (U/μg) |
|---|---|---|
| TNF-32D | 5.5 | 1.1 |
| TNF-32S | 5.8 | 1.0 |
| TNF-32G | 5.8 | 8.7 |
| TNF-32L | 5.8 | 0.43 |
| TNF-36V | 5.9 | 122 |
| TNF-73P | 6.0 | 234 |
| TNF-98H | 6.4 | 1,330 |
| TNF-103P | 6.2 | 215 |
| TNF-115L | 5.9 | 12 |
| TNF-115S | 5.8 | 23 |
| TNF-115T | 5.8 | 38 |
| TNF-115H | 6.0 | 220 |
| TNF-115R | 7.0 | 0.22 |
| TNF-115D | 5.7 | 6.8 |
| TNF-115G | 5.9 | 37 |
| TNF-117H | 6.3 | 31 |
| TNF-131I | 5.9 | 1,890 |
| TNF-143V | 5.8 | 243 |
| TNF-144K | 7.5 | 1.3 |
| TNF-146E | 5.6 | 0.18 |
| TNF-115LΔN8 | 5.9 | 10 |

(3) Table 5 shows the antitumor activities in vivo of human TNF (as a control) and the various human TNF polypeptide mutants obtained in Examples given hereinbelow. The antitumor activity was evaluated as follows:

Meth A sarcoma cells (2×10⁵) were transplanted into the abdominal skin of BALB/c female mice (8 week old). Seven days after the transplantation, the polypeptide was administered once intravenously. The tumor necrotizing response was evaluated 24 hours after the administration by the evaluation standards of Carswell et al. [Proc. Natl. Acad. Sci. USA, 72, 3666 (1975)].

As shown in Table 5, the correlation between the cytotoxic activity in vitro and the antitumor activity in vivo against the transplanted tumor is scarce. For example, TNF-131I has nearly the same in vitro cytotoxic activity and in vivo antitumor activity as those of human TNF. However, other human TNF polypeptide mutants, for example human TNF polypeptide mutant in which the 32nd, 115th or 143rd amino acid from the N-terminus is replaced, show strong in vivo antitumor activity as compared with their in vitro cytotoxic activity, and have low lethal toxicity.

TABLE 5

Antitumor Effect of Human TNF Polypeptide Mutant on Meth A Sarcoma Transplanted in Mice:

| Polypeptide: dose (unit)/mouse | Necrotic Response − | + | + + | + + + | Inhibition of Tumor Growth (%) |
|---|---|---|---|---|---|
| Human TNF: | | | | | |
| 600 | 1 | 5 | 0 | 0 | 55 |
| 2,000 | 0 | 4 | 2 | 0 | 80 |
| 6,000 | 0 | 0 | 6 | 0 | 87 |
| 20,000 | 0 | 0 | 0 | 6 | 100 |
| TNF-16V: | | | | | |
| 93 | 6 | 0 | 0 | 0 | 61 |
| 310 | 4 | 2 | 0 | 0 | 64 |
| 930 | 0 | 4 | 2 | 0 | 90 |
| 3,100 | 0 | 0 | 6 | 0 | 86 |
| 9,300 | 0 | 0 | 3 | 3 | 100 |
| TNF-31T: | | | | | |
| 35 | 7 | 0 | 0 | 0 | 49 |
| 115 | 2 | 5 | 0 | 0 | 79 |
| TNF-32Y: | | | | | |
| 5 | 4 | 3 | 0 | 0 | 26 |
| 18 | 3 | 4 | 0 | 0 | 46 |
| TNF-32D: | | | | | |
| 11 | 4 | 0 | 0 | 0 | 63 |
| 33 | 0 | 5 | 0 | 0 | 82 |
| 110 | 0 | 1 | 3 | 1 | 81 |
| TNF-32S: | | | | | |
| 10 | 5 | 0 | 0 | 0 | 17 |
| 30 | 1 | 4 | 0 | 0 | 68 |
| 100 | 0 | 1 | 4 | 0 | 97 |
| TNF-32H: | | | | | |
| 32 | 4 | 1 | 0 | 0 | 45 |
| 96 | 1 | 4 | 0 | 0 | 73 |
| 320 | 0 | 3 | 2 | 0 | 100 |
| TNF-36V: | | | | | |
| 120 | 2 | 4 | 0 | 0 | 49 |
| 370 | 0 | 4 | 2 | 0 | 83 |
| 1,200 | 0 | 0 | 2 | 4 | 93 |
| 3,700 | 0 | 0 | 0 | 6 | 93 |
| TNF-73P: | | | | | |
| 230 | 5 | 2 | 0 | 0 | 8 |
| 700 | 0 | 7 | 0 | 0 | 66 |
| 2,300 | 0 | 5 | 2 | 0 | 90 |
| TNF-98H: | | | | | |
| 1,300 | 2 | 5 | 0 | 0 | 70 |
| 4,000 | 0 | 5 | 2 | 0 | 81 |
| 13,000 | 0 | 0 | 1 | 6 | 94 |
| TNF-103P: | | | | | |
| 215 | 0 | 1 | 6 | 0 | 70 |
| 645 | 0 | 0 | 4 | 3 | 100 |
| TNF-115L: | | | | | |
| 12 | 5 | 1 | 0 | 0 | 70 |
| 35 | 2 | 4 | 0 | 0 | 73 |
| 117 | 0 | 5 | 1 | 0 | 78 |
| 350 | 0 | 2 | 4 | 0 | 91 |
| 1,170 | 0 | 0 | 5 | 1 | 93 |
| TNF-115S: | | | | | |
| 23 | 3 | 3 | 0 | 0 | 74 |
| 69 | 0 | 4 | 2 | 0 | 81 |
| 230 | 0 | 2 | 4 | 0 | 91 |
| 690 | 0 | 0 | 5 | 1 | 84 |
| 2,300 | 0 | 0 | 1 | 5 | 100 |
| TNF-115H: | | | | | |
| 220 | 5 | 1 | 0 | 0 | 72 |
| 660 | 0 | 5 | 1 | 0 | 80 |
| 2,200 | 0 | 1 | 5 | 0 | 96 |
| TNF-115T: | | | | | |
| 38 | 2 | 3 | 0 | 0 | 54 |
| 114 | 2 | 3 | 0 | 0 | 83 |
| 380 | 1 | 2 | 2 | 0 | 91 |
| 1,140 | 0 | 0 | 5 | 0 | 100 |
| TNF-115D: | | | | | |
| 68 | 0 | 5 | 0 | 0 | 57 |
| 204 | 0 | 2 | 3 | 0 | 100 |
| TNF-115G: | | | | | |
| 110 | 0 | 5 | 0 | 0 | 68 |
| 370 | 0 | 1 | 4 | 0 | 98 |
| 1,100 | 0 | 0 | 1 | 4 | 100 |
| TNF-117H: | | | | | |
| 31 | 4 | 3 | 0 | 0 | 51 |
| 92 | 1 | 6 | 0 | 0 | 88 |
| 310 | 0 | 0 | 7 | 0 | 93 |
| TNF-131I: | | | | | |
| 5,700 | 0 | 0 | 2 | 3 | 83 |
| 19,000 | 0 | 0 | 1 | 3 | 98 |
| TNF-143V: | | | | | |
| 730 | 0 | 5 | 0 | 0 | 42 |
| 2,400 | 0 | 4 | 1 | 0 | 65 |
| 7,300 | 0 | 1 | 3 | 1 | 100 |

(4) Several human TNF polypeptide mutants of this invention as well as human TNF were tested for pyrogenicity in rabbit. The results are shown in Table 6.

The pyrogenicity test was carried out by administering the polypeptide intravenously to rabbit, and observing change in the rectal temperature for 4 hours after the administration. The results are expressed as follows:
(−): a rectal temperature rise of not more than 0.4° C.
(+): a rectal temperature rise of 0.5 to 0.9° C.
(++): a rectal temperature rise of 1.0° C. or more

TABLE 6

| Pyrogenicity of Human TNF Polypeptide Mutant in Rabbit: | | |
|---|---|---|
| Polypeptide: | dose (μg/kg) | Pyrogenicity |
| Human TNF: | 0.50 | (+) |
| TNF-16V: | 0.52 | (−) |
|  | 5.2 | (−) |
|  | 52 | (+) |
| TNF-32Y: | 0.56 | (−) |
|  | 5.6 | (−) |
|  | 56 | (−) |
| TNF-32H: | 0.50 | (−) |
|  | 5.0 | (−) |
|  | 50 | (−) |
| TNF-36V: | 0.50 | (−) |
|  | 5.0 | (+) |
|  | 50 | (+) |
| TNF-73P: | 0.51 | (−) |
|  | 5.1 | (+) |
|  | 51 | (++) |
| TNF-115L: | 0.67 | (−) |
|  | 6.7 | (−) |
|  | 67 | (+) |
| TNF-115S: | 0.52 | (−) |
|  | 5.2 | (+) |
|  | 52 | (+) |
| TNF-115H: | 0.50 | (−) |
|  | 5.0 | (+) |
|  | 50 | (+) |
| TNF-117H: | 0.52 | (−) |
|  | 5.2 | (−) |
|  | 52 | (+) |

(5) The effect of the polypeptide mutant (TMF-115L) on the blood pressure was tested by administering into the tail vein of SHR/NCrj male rats (body weight (b 264 to 204 g; Nippon Charles River Co., Ltd.), and measuring the systolic blood pressure of the rats without anesthesia by means of an arterial pressure measuring device for rats (Model KN-209, made by Natsume Seisakusho). As a control human TNF was administered as well.

The results are shown in Table 7.

TABLE 7

| Effect of TNF-115L on Blood Pressure in Rats | | | |
|---|---|---|---|
| Polypeptide dosage | Changes in Blood Pressure (mean ± SD) (hours after Administration) | | |
| (μg/kg) | before | 5 hours | 24 hours |
| Human TNF: 100 | 193±3.1 mmHg | 183±2.0 mmHg | 170±3.2 mmHg |
| TNF-115L: | | | |
| 100 | 189±3.0 mmHg | 195±2.5 mmHg | 191±2.6 mmHg |
| 1,000 | 189±3.0 | 178±2.7 | 184±2.2 |
| 5,000 | 190±1.5 | 186±2.1 | 189±2.5 |
| 10,000 | 191±2.1 | 185±2.4 | 188±3.6 |

For formulating human TNF polypeptide mutants of this invention, they may be in the form of a solution or a lyophilized product. From the standpoint of long-term stability, they are desirably in the form of lyophilized products. It is preferred to add vehicles or stabilizers to the preparations. Examples of the stabilizers include albumin, globulin, gelatin, protamine, protamine salts, glucose, galactose, xylose, mannitol, glucuronic acid, trehalose, dextran, hydroxyethyl starch, and non-ionic surface-active agents (such as plyoxyethylene fatty acid esters, polyoxyethylene alkyl ethers, polyoxyethylene alkyl phenyl ethers, polyoxyethylene sorbitan fatty acid esters, polyoxyethylene glycerin fatty acid esters, polyoxyethylene hardened castor oil, polyoxyethylene castor oil, polyoxyethylene polyoxypropylene alkyl ethers, polyxoyethylene polyoxypropylene block copolymer, sorbitan fatty acid esters, sucrose fatty acid esters and glycerin fatty acid esters).

The several human TNF polypeptide mutants of this invention are especially useful as antitumor agents as shown above.

Such polypeptide preparations are preferably administered parenterally or topically. Parenteral routes such as intraveous and intramuscular routes are used when tumor cells extend over a wide range or metastasize, or when prevention of metastasis is intended. Against local tumor tissues, direct intratumor administration is preferred. The dosage varies depending upon the type of human TNF polypeptide mutants and the type and size of tumors, the condition of the patient and the route of administration. For example, in case of TNF-115L, it is $1 \times 10^3$ to $1 \times 10^8$ units (LM)/kg, preferably $1 \times 10^4$ to $1 \times 10^7$ units (LM)/kg.

The following examples illustrate the present invention more specifically. It should be understood however that other human TNF polypeptide mutants in accordance with this invention can also be produced by similar methods, and the invention is in no way limited to these examples.

EXAMPLE 1

Production of Human TNF Polypeptide Mutant TNF-32Y (1) Construction of an expression plasmid An expression plasmid (pHNY-32) for producing a polypeptide consisting of 155 amino acids corresponding to the sequence from amino acid No. 1 to No. 155 in Table 9 hereinbelow, referred to as TNF-32Y, was constructed as illustrated in FIGS. 2 and 3.

A cloned cDNA encoding human TNF was isolated by digestion with restriction endonuclease PstI from the recombinant plasmid pHTNF13 prepared according to the method described in European Patent Publication No. 155549.

The cloned cDNA was further digested with restriction endonucleases AvaI and HindIII to isolate a DNA fragment containing most of the coding region for the human TNF polypeptide. The isolated DNA fragment is referred to as TNF-DNA fragment.

The TNF-DNA fragment was about 600 bp in size containing the base sequence corresponding to the downstream region from base No. 250 in Table 8. Its full base sequence was reported by Yamada et al. [J. Biotechnology, 3, 141 (1985)].

The TNF-DNA fragment was further digested with restriction endonucleases HpaII and BglI to cut it into three DNA fragment and they were isolated. These DNA fragments had the sequences corresponding to the region from base No. 250 to No. 321, the region from base No. 322 to 337 and the downstream region from base No. 338 in Table 8, respectively. These DNA fragments were named DNA-1 fragment, DNA-2 fragment and DNA-3 fragment, respectively.

Then, the DNA-1 and DNA-3 fragments were combined by using T4 DNA ligase with the following chemically synthesized oligodeoxyribonucleotide adapter [a].

```
5'-CGGGCCTATGCCCTCC-3'           [a]
3'-CCGGATACGGG-5'
```

The ligated DNA fragment is referred to as NY-DNA fragment. The NY-DNA fragment was sequentially ligated with the following two chemically synthesized oligodeoxyribonucleotide adapters, [b] and [c].

```
5'-AACTAGTACGCAAGTTCACGTAAGGAGGTTATC-3'           [b]
3'-TTGATCATGCGTTCAAGTGCATTCCTCCAATAGCTA-5'
``` and

```
5'-GATTATGTCATCTTCTCGAACC-3'           [c]
3'-ATACAGTAGAAGAGCTTGGGGCT-5'
```

The resulting DNA fragment is referred to as Peptide coding-DNA fragment.

A DNA fragment (about 380 bp in size) containing the trp promoter region was isolated from a plasmid pCT-1 [M. Ikehara et al., Proc. Natl. Acad. Sci., USA, 81, 5956 (1984)] by double digestion with restriction endonucleases HpaI and AatII. The base sequence of the trp promoter region of the above 380 bp-DNA fragment was reported by Bennett et al. [J. Mol. Biol., 121, 133 (1978)]. The above 380 bp-DNA fragment was ligated with the Peptide coding-DNA fragment prepared as above. The ligated DNA fragment was referred to as Promoter-Peptide coding-DNA fragment.

Separately, a plasmid pBR322 was digested with restriction endonucleases AvaI and PvuII, and the resulting larger DNA fragment (about 3.7 kbp in size) was isolated by 0.7% agarose gel electrophoresis. After filling in its cohesive ends to blunt ends with *E. coli* DNA polymerase I (Klenow fragment) and four kinds of deoxyribonucleotide triphosphates (dGTP, dATP, dTTP and dCTP), both ends were ligated by T4 DNA ligase to construct a new plasmid, which is designated pBRS6.

The plasmid pBRS6 was cleaved with restriction endonucleases AatII and HindIII into two DNA fragments. The larger DNA fragment (about 3.6 kbp in size) was isolated and ligated by T4 DNA ligase with the Promoter-Peptide coding-DNA fragment prepared as above in order to construct an expression plasmid pHNY-32.

(2) Production of TNF-32Y

The expression plasmid pHNY-32 was introduced into *E. coli* HB101 by the conventional method [S. N. Cohen et a., Proc. Natl. Acad. Sci., USA, 69, 2110 (1972)].

The transformant (HB101/pHNY-32) was cultivated at 37° C. overnight in LB broth [composition: 1% trypton, 0.5% yeast extract, 1% naCl, pH 7.5]. The culture was inoculated in 10-volumes of modified M9 medium [composition: 1.5% $Na_2HPO_4 \cdot 12H_2O$, 0.3% $KH_2PO_4$, 0.05% NaCl, 0.1% $NH_4Cl$, 2 mg/liter of vitamin B1, 0.45% casamino acid, 1 mM $MgSO_4$, 0.1 mM $CaCl_2$ and 0.4% glycerol] containing ampicillin at 25 micrograms/ml, at 37° C. for 1 hour.

Then, 3-indoleacrylic acid was added to give a final concentration of 20 micrograms/ml. After the cultivation was further continued for 24 hours, the cells were collected by centrifugation. THe cells were suspended in 50 mM Tris-HCl buffer (pH 8) containing 0.1% lysozyme and 30 mM NaCl, and allowed to stand in an ice bath for 30 minutes. After the cell suspension was repeatedly treated by freezing in a dry ice/ethanol bath and thawing at 37° C., the cell extract was collected by centrifugation.

The cell extract was dialyzed against 20 mM Tris-HCl buffer (pH 7.8), and the dialyzate was centrifuged to obtain a clarified supernatant. The supernatant was applied onto a DEAE-Sepharose CL-6B column (Pharmacia) previously equilibrated with 20 mM Tris-HCl buffer (pH 7.8). After the column was washed with the same buffer to remove non-adsorbed components, the desired polypeptide (TNF-32Y) was eluted with a linear gradient of NaCl concentration from zero to 0.3 M in the same buffer. Each fraction was subjected to SDS-polyacrylamide gel electrophoresis, and the fractions containing polypeptide having a molecular weight of about 17 kilodaltons were collected and pooled.

The pooled fraction was dialyzed against 20 mM Tris-HCl buffer (pH 7.8), and then it was again subjected to DEAE-Sepharose CL-6B column chromatography as above, but the elution was carried out under the elution condition of an easier gradient of NaCl concentration.

The fractions containing the desired polypeptide were collected, pooled and concentrated by ultrafiltration with Diaflo using a YM10 membrane (Amicon).

Finally, the concentrate was subjected to gel filtration on a column of Bio-Gel P-6 (Bio-Rad) using 5 mM phosphate buffered saline as an eluent to obtain purified TNF-32Y.

N-terminal amino acid sequence of the purified TNF-32Y was analyzed by the automated Edman degradation on Protein Sequencer (Applied Biosystems, Model 470A).

As a result, the N-terminal amino acid of TNF-32Y was a serine residue. Namely, a methionine residue due to the translation initiation codon (ATG) was removed from the purified product.

EXAMPLE 2

Figure 4:
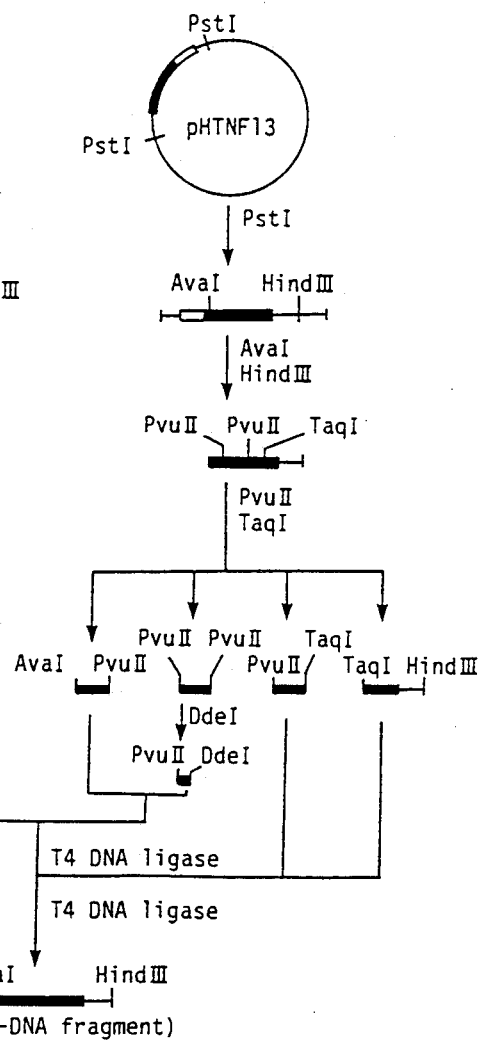
FIG. 4 shows the steps of preparing a PL-DNA fragment for construction of an expression plasmid pHPL-115 (in Example 2)

Production of Human TNF Polypeptide Mutant TNF-115L (1) Construction of an expression plasmid An expression plasmid (pHPL-115) for producing a polypeptide consisting of 155 amino acids corresponding to the sequence of the amino acid No. 1 to No. 155 in Table 10 attached, referred to as TNF-115L, was constructed as illustrated in FIG. 4.

The TNF-DNA fragment prepared as mentioned in Example 1-(1) was digested with restriction endonucleases PvuII and TaqI to cut it into four DNA fragments and they were isolated. These DNA fragments had the sequences corresponding to the region from base No. 250 to 369, the region from base No. 370 to 603, the region from base No. 604 to No. 653 and the downstream region from base No. 654 in Table 8, respectively.

These DNA fragments were named DBNA-4 fragment, DNA-5 fragment, DNA-6 fragment and DNA-7 fragment, respectively. The DNA-5 fragment was further digested with restriction endonuclease DdeI to isolate a DNA fragment corresponding to the sequence from base No. 370 to No. 554 in Table 8 (referred to as DNA-8 fragment).

The DNA-8 fragment was combined with the DNA-4 fragment, and then ligated with the following two chemically synthesized oligodeoxyribonucleotide adapters, [d] and [e].

[d]

and

[e]

To the ligated DNA fragment, the DNA-6 fragment and the DNA-7 fragment were further ligated by using T4 DNA ligase. The resulting DNA fragment is referred to as PL-DNA fragment.

The expression plasmid pHPL-115 was constructed according to the method as mentioned in Example 1-(1), except for using the PL-DNA fragment instead of the NY-DNA fragment.

(2) Production of TNF-115L

According to the method mentioned in example 1-(2), the transformant (HB101/pHPL-115) was prepared and cultivated. The desired polypeptide was isolated and purified from the cell extract according to essentially the same method as mentioned in Example 1-(2).

(3) Determination of amino acid sequence

Amino acid sequences of the purified TNF-115L and its peptide fragment were analyzed by the automated Edman degradation on a Protein Sequencer.

Figure 5:
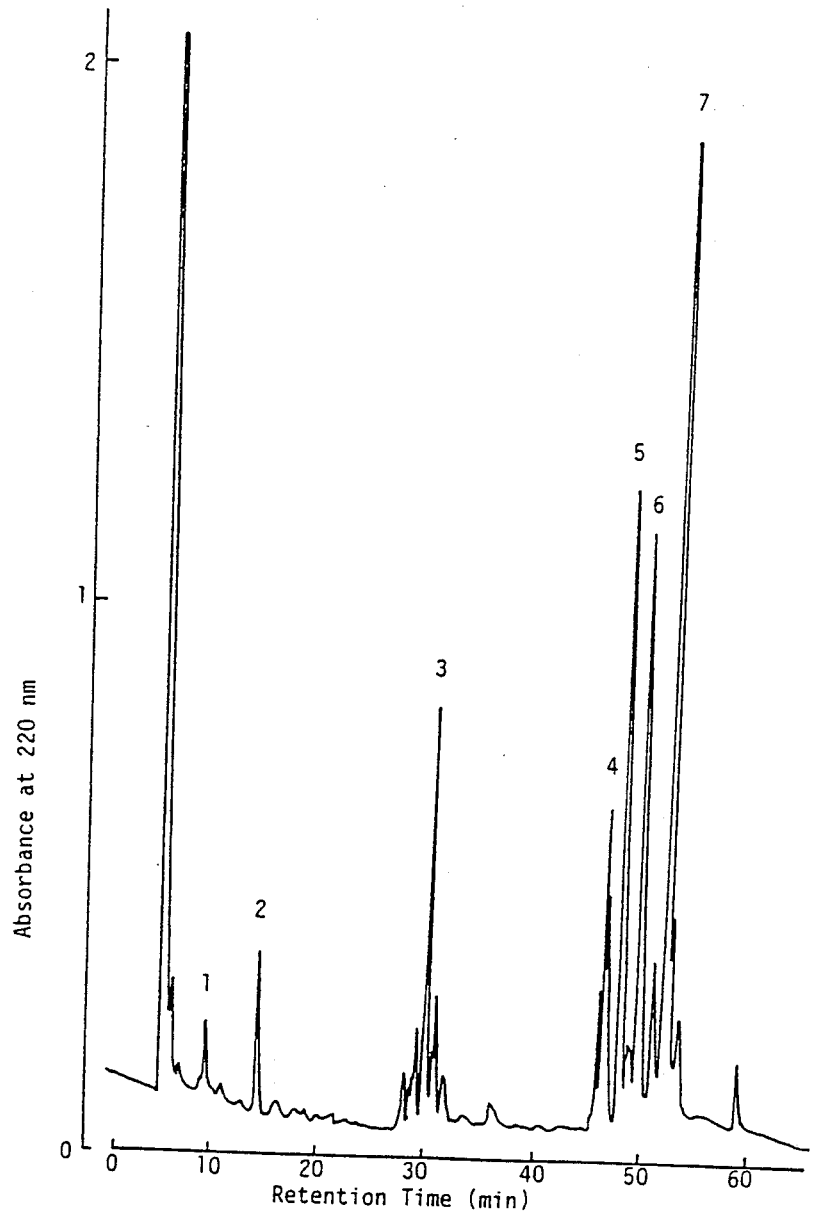
FIG. 5 shows an elution pattern by high performance liquid chromatography of peptide fragments from polypeptide TNF-115L by digestion with lysyl endopeptidase (in Example 2)

The peptide fragment was prepared under the following conditions. Five hundred micrograms of the purified TNF-115L was incubated with 10 micrograms of lysyl endopeptidase (EC 3.4.21.50: Wako Pure Chemical Ind.) in 5 mM Tric-HCl buffer (pH 8) containing 4M urea in a total volume of 0.1 ml. After incubation at 35° C. for 15 hours, the resulting digested peptides were isolated by high performance liquid chromatography using a column of SynChropak RP-P300 (250×4.6 mm; SynChrom Inc.) under the conditions of a linear gradient elution from 10% to 50% of acetonitrile containing 0.07% trifluoroacetic acid, in 0.1% trifluoroacetic acid, at a flow rate of 1 ml/min for 60 minutes. The elution pattern is shown in FIG. 5. The peptide fragments were isolated from each of fractions of No. 1 to No. 7 in FIG. 5 and subjected to analysis of amino acid sequence by the automated Edman degradation method.

The partial amino acid sequence of peptide fragment No. 6 was determined to be Pro-X-Try-Glu-Leu-Ile-Tyr-Leu-Gly-Gly-Val-Phe-Gln-Leu-Glu. Mark "X" shows an amino acid which could not be determined by this analysis.

The determined amino acid sequence as above was completely agreed with the sequence from amino acid No. 111 to No. 125 in Table 10.

It was confirmed that the amino acid at the 115th position from the N-terminus of TNF-115l was a leucine residue.

N-terminal amino acid of the purified TNF-115L was a serine residue, indicating that a methionine residue due to the translation initiation codon (ATG) was removed.

EXAMPLE 3

Production of Human TNF Polypeptide Mutant TNF-115LΔN8

(1) Construction of an expression plasmid

Figure 6:
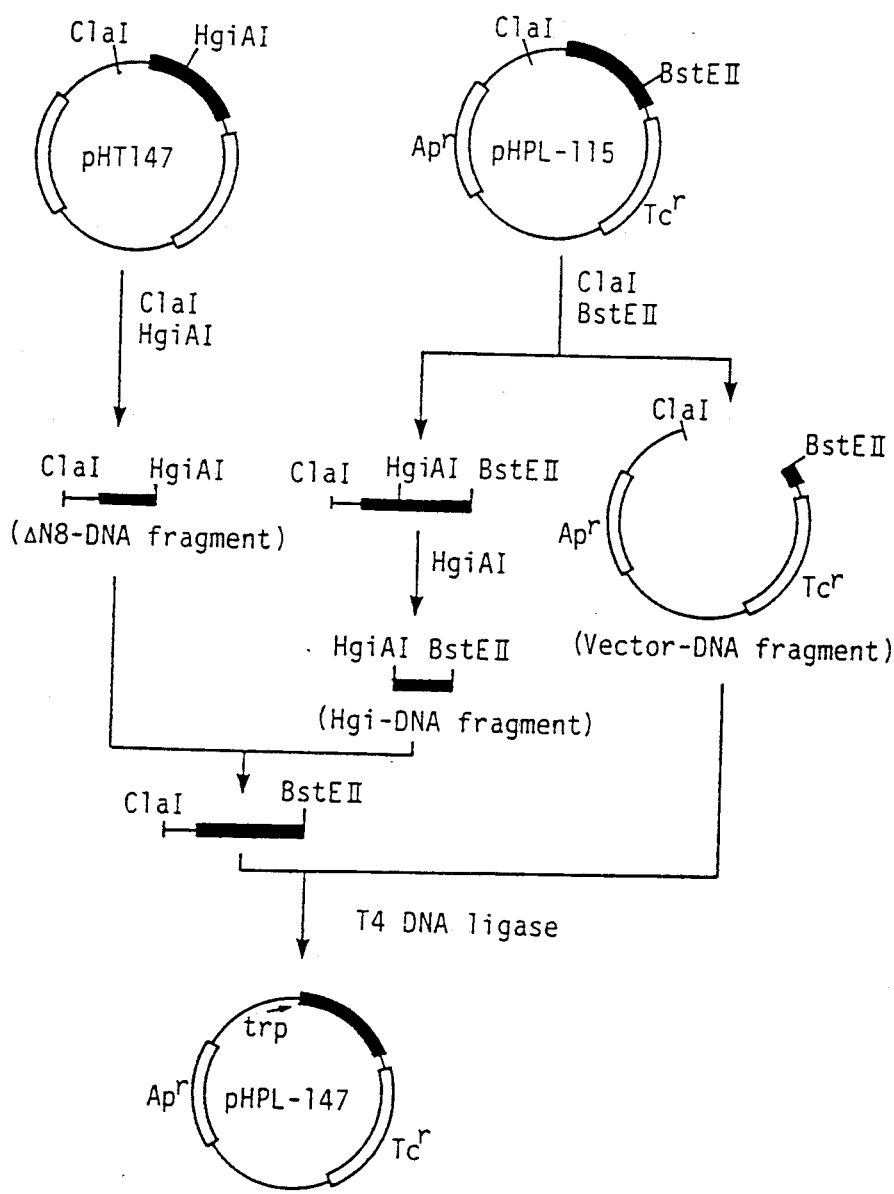
FIG. 6 shows the steps of constructing an expression plasmid pHPL-147 (in Example 3)

An expression plasmid (pHPL-147) for producing a polypeptide consisting of 147 amino acids corresponding to the sequence from amino acid No. 9 (Lys) to No. 155 (Leu) in Table 10, referred to as TNF-115LΔN8, was constructed as illustrated in FIG. 6.

The expression plasmid pHPL-115 prepared as mentioned in Example 2-(1) was cut into two DNA fragments by digestion with restriction endonucleases ClaI and BstEII. The larger fragment contains the downstream region from base No. 380 in Table 10 (coding region for C-terminal portion of TNF-115L), tetracycline-resistance gene, ampicillin-resistance gene and the trp promoter region, which is referred to as Vector-DNA fragment.

The smaller fragment contains the region corresponding to the sequence from base No. 1 to No. 379 in Table 10. This fragment was further digested with restriction endonuclease HgiAI to isolate a DNA fragment corresponding to the sequence from the base No. 219 to No. 379, which is referred to as Hgi-DNA fragment.

Separately, the expression plasmid pHT147 prepared as mentioned in Referential example 2, was digested with restriction endonucleases ClaI and HgiAI to isolate a DNA fragment (about 200 bp in size) containing the region corresponding tot he sequence from base No. 25 to No. 218 in Table 10. This DNA fragment is referred to as ΔN8-DNA fragment.

The ΔN8-DNA fragment was ligated with the Hgi-DNA fragment by using T4 DNA ligase, and then the ligated DNA fragment was combined with the Vecotr-DNA fragment prepared as above to construct the expression plasmid pHPL-147.

(2) Production of TNF-115LΔN8

According to the method as mentioned in Example 1-(2), the transformant (HB101/pHPL-147) was prepared and cultivated. The desired polypeptide was isolated and purified from the cell extract according to essentially the same method as mentioned in Example 1-(2).

At the N-terminus of purified TNF-115LΔN8, a methionine residue due to the translation initiation codon (ATG) was detected by the automated Edman degradation method.

EXAMPLE 4

Production of Human TNF Polypeptide Mutant TNF-115L-Ser67

(1) Construction of an expression plasmid

Figure 7:
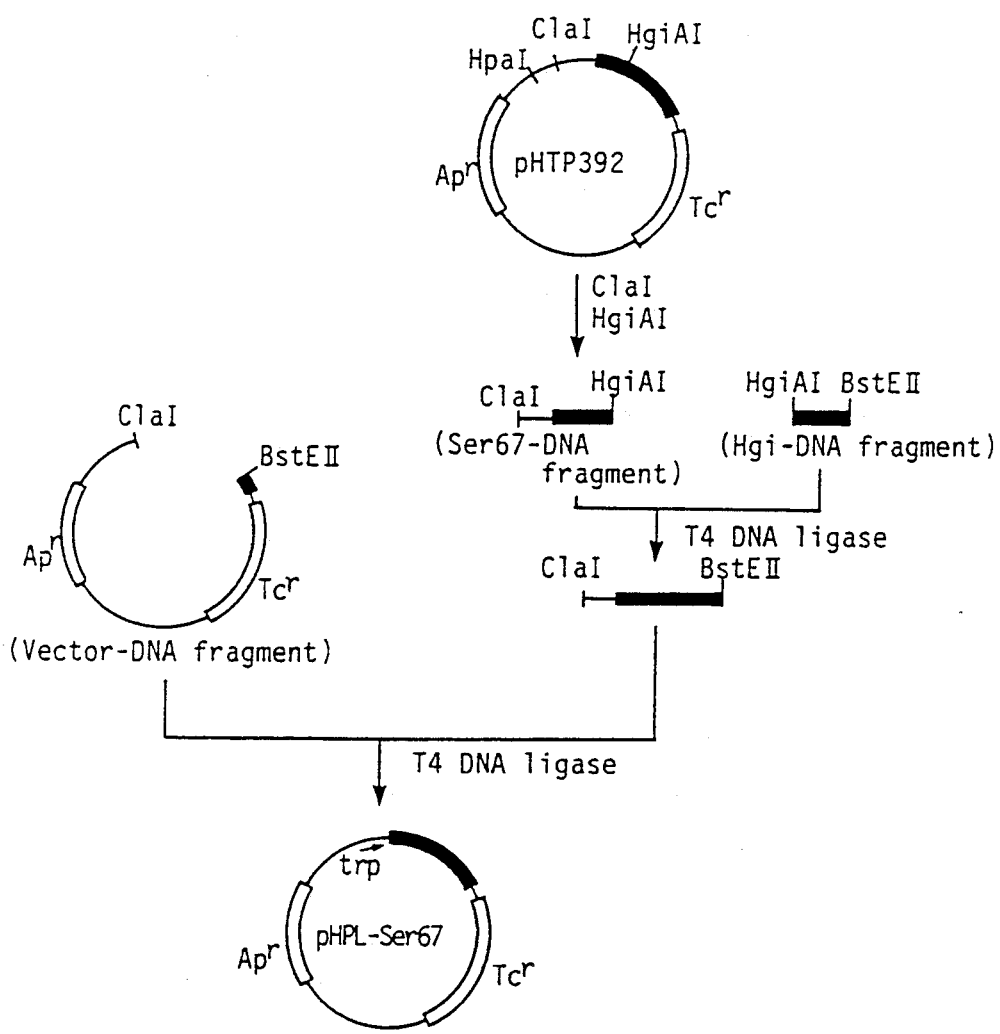
FIG. 7 shows the steps of constructing an expression plasmid pHPL-Ser67 (in Example 4)

An expression plasmid (pHPL-Ser67) for producing a polypeptide consisting of 155 amino acids and having an amino acid sequence corresponding to the sequence from amino acid No. 1 to No. 155 in TAble 10, in which a cysteine residue at amino acid No. 67 was replaced by a serine residue, referred to as TNF-115L-Ser67, was constructed as illustrated in FIG. 7.

The expression plasmid pHTP392 prepared as mentioned in Referential Example 3 was digested with restriction endonucleases ClaI, HgiAI and HpaI to isolate a DNA fragment (about 226 bp in size) containing the base sequence from base No. 1 to No. 218 in Table 10, but in which two bases at base Nos. 200 and 201 in Table 10, G and C, were replaced by C and T, respectively. The DNA fragment is referred to as SER67-DNA fragment.

The Ser67-DNA fragment was ligated with the Ghi-DNA fragment prepared as mentioned in Example 3-(1), and the ligated DNA fragment was combined with the Vecotr-DNA fragment prepared as mentioned in Example 3-(1), in order to construct the expression plasmid pHPL-Ser67.

(2) Production of TNF-115L-Ser67

According to the method as mentioned in example 1-(2), the transformant (HB101/pHPL-Ser67) was prepared and cultivated. The desired polypeptide was isolated and purified from the cell extract by essentially the same method as mentioned in Example 1-(2).

A methionine residue due to the translation initiation codon (ATG) was not detected at the N-terminus of purified TNF-115L-Ser67 by the automated Edman degradation method. The N-terminal amino acid was serine residue.

EXAMPLE 5

Production of Human TNF Polypeptide Mutant TNF-115LΔN8-Ser67

(1) Construction of an expression plasmid

Figure 8:
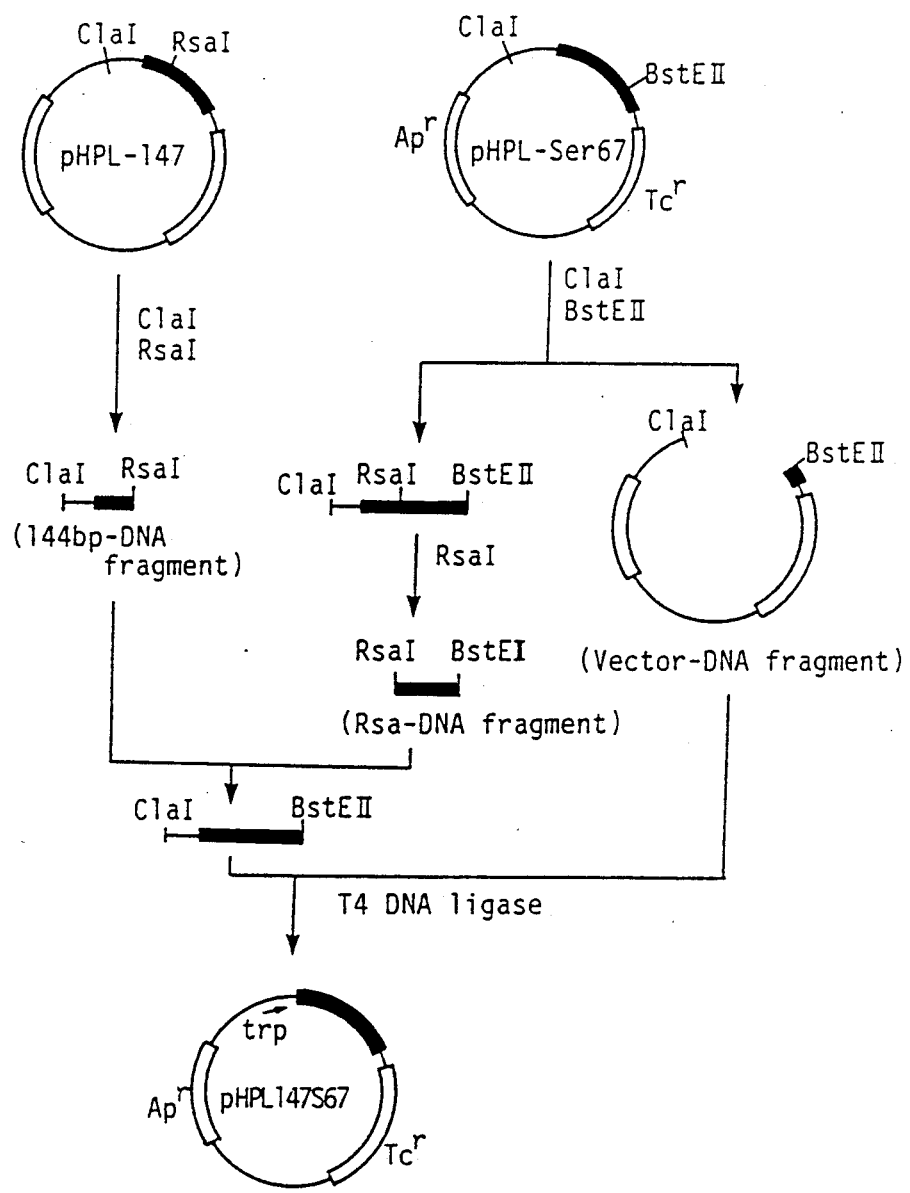
FIG. 8 shows the steps of constructing an expression plasmid pHPL147S67 (in Example 5)

An expression plasmid (pHPL147S67) for producing a polypeptide consisting of 147 amino acids and having an amino acid sequence corresponding to the sequence from amino acid No. 9 to No. 155 in Table 10, in which a cysteine residue in amino acid No. 67 was replaced by a serine residue, referred to as TNF-115LΔN8-Ser67, was constructed as illustrated in FIG. 8.

The expression plasmid pHPL-Ser67 prepared as mentioned in Referential Example 4-(1) was digested with restriction endonucleases ClaI and BstEII to cleave two fragments. The larger DNA fragment is the same fragment with the Vector-DNA fragment prepared in Example 3. The smaller DNA fragment was further digested with restriction endonuclease RsaI to isolate a DNA fragment containing the base sequence from base No. 161 to No. 379 in Table 10, which is referred to as Rsa-DNA fragment.

Separately, the expression plasmid pHPL-147 prepared as mentioned in Example 3-(1) was digested with restriction endonucleases ClaI and RsaI to isolate a DNA fragment (about 144 bp in size) containing the base sequence from base No. 25 to No. 160 in Table 10. The 144 bp-DNA fragment prepared as above was ligated with the Rsa-DNA fragment by T4 DNA ligase, and the resulting DNA fragment was combined with the Vector-DNA fragment to construct the expression plasmid, pHPL147S67, for producing TNF-115LΔN8-Ser67.

(2) Production of TNF-115LΔN8-Ser67

According to the method as mentioned in example 1-(2), the transformant (HB101/pHPL147S67) was prepared and cultivated. The desired polypeptide was isolated from the cell extract and purified according to essentially the same method as mentioned in Example 1-(2).

A methionine residue due to the translation initiation codon (ATG) was detected at the N-terminus of purified TNF-115LΔN8-Ser67 by the automated Edman degradation method.

EXAMPLE 6

Production of Other Human TNF POlypeptide Mutants-1

(1) Construction of expression plasmids

An expression plasmid for producing a polypeptide consisting of 155 amino acids and having an amino acid sequence corresponding to the sequence from amino acid No. 1 to No. 155 in Table 1, in which an asparagine residue in the 32nd position from the N-terminus was replaced by another amino acid, for example, His, Asp and Ser, was constructed according to the method as mentioned in example 1-(1), except for using one of the chemically synthesized oligodeoxyribonucleotide adapters shown below instead of the synthetic adapter [a]:

```
5'-CGGGCCCACGCCCTCC-3'
   3'-CCGGGTGCGGG-5'
   (for replacement by His),

5'-CGGGCCGATGCCCTCC-3'
   3'-CCGGCTACGGG-5'
   (for replacement by Asp), or

5'-CGGGCCAGCGCCCTCC-3'
   3'-CCGGTCGCGGG-5'
   (for replacement by Ser).
```

(2) Production of human TNF polypeptide mutant

Each of the expression plasmids obtained in Section (1) was introduced in *E. coli* Hb101 by the conventional method, and the transformant was cultivated according to the method described in example 1-(2).

The desired polypeptide was purified from the cell extract by essentially the same method as mentioned in example 1-(2).

There were obtained the following human TNF polypeptide mutants.

TNF-32H: Polypeptide having an amino acid sequence of formula [I] in which 32nd Asn was replaced by His.

TNF-32D: Polypeptide having an amino acid sequence of formula [I] in which 32nd Asn was replaced by Asp.

TNF-32S: Polypeptide having an amino acid sequence of formula [I] in which 32nd Asn was replaced by Ser.

EXAMPLE 7

Production of Other Human TNF Polypeptide Mutants-2

(1) Construction of expression plasmids

An expression plasmid for producing a polypeptide consisting of 155 amino acids and having an amino acid sequence corresponding to the sequence from amino acid No. 1 to No. 155 in Table 1, in which a proline residue in the 115th position from the N-terminus was replaced by another amino acid, for example, Ser, Asp and Gly, was constructed according to the method as mentioned in Example 2-(1), except for using one of the chemically synthesized oligodeoxyribonucleotide adapters shown below instead of the synthetic adapter [d]:

5'-TGAGGCCAAGCCCTGGTATGAGTCCAT-3'
3'-CCGGTTCGGGACCATACTCAG-5'
(for replacement by Ser), 5'-TGAGGCCAAGCCCTGGTATGAGGACAT-3'
3'-CCGGTTCGGGACCATACTCCT-5'
(for replacement by Asp), or 5'-TGAGGCCAAGCCCTGGTATGAGGGCAT-3'
3'-CCGGTTCGGGACCATACTCCC-5'
(for replacement by Gly).

(2) Production of human TNF polypeptide mutants

Each of the expression plasmids obtained in Section (1) was introduced in *E. coli* HB101 by the conventional method, and the transformant was cultivated according to the method described in example 1-(2).

The desired polypeptide was isolated and purified from the cell extract by essentially the same method as described in example 1-(2).

There were obtained the following human TNF polypeptide mutants.

TNF-115S: Polypeptide having an amino acid sequence of formula [I] in which 115th Pro was replaced by Ser.

TNF-115D: Polypeptide having an amino acid sequence of formula [I] in which 115th Pro was replaced by Asp.

TNF-115G: Polypeptide having an amino acid sequence of formula [I] in which 115th Pro was replaced by Gly.

EXAMPLE 8

Production of Human TNF Polypeptide Mutant TNF-117H, referred to as TNF-117H (1) Construction of expression plasmids An expression plasmid for producing a polypeptide consisting of 155 amino acids and having an amino acid sequence corresponding to the sequence from amino acid No. 1 to No. 155 in Table 1, in which a tyrosine residue in the 117th position from the N-termnus was replaced by another amino acid, for example, His, was constructed according to the method as mentioned in Example 2-(1), except for using a chemically synthesized oligodeoxyribonucleotide adapter shown below instead of the synthetic adapter [e]:

5'-CCATCTGGGAGGGGTCTTCCAG-3'
3'-GTAGGTAGACCCTCCCCAGAAGGTC-5'

(2) Production of TNF-117H

The expression plasmid obtained in Section (1) was introduced in *E. coli* HB101 by the conventional method, and the transformant was cultivated according to the method described in Example 1-(2).

The desired polypeptide was isolated and purified from the cell extract by essentially the same method as mentioned in example 1-(2).

EXAMPLE 9

Production of Other Human TNF Polypeptide Mutants-3

In accordance with example 1, expression plasmids for production of the following polypeptides were constructed. *Escherichia coli* was transformed with the expression plasmids. The transformants were cultured, and the polypeptides were isolated and purified.

TNF-16V: Polypeptide having an amino acid sequence of formula [I] in which 16th Ala was replaced by Val TNF-31T: Polypeptide having an amino acid sequence of formula [I] in which 31st Ala was replaced by Thr TNF-32G: Polypeptide having an amino acid sequence of formula [I] in which 32nd Asn was replaced by Gly TNF-32L: Polypeptide having an amino acid sequence of formula [I] in which 32nd Asn was replaced by Leu TNF-36V: Polypeptide having an amino acid sequence of formula [I] in which 36th Ala was replaced by Val TNF-73P: Polypeptide having an amino acid sequence of formula [I] in which 73rd Leu was replaced by Pro TNF-82D: Polypeptide having an amino acid sequence of formula [I] in which 82nd Ala was replaced by Asp pI 5.3 (its isoelectoric point was 5.3)

TNF-85H: Polypeptide having an amino acid sequence of formula [I] in which 85th Tyr was replaced by His pI 6.4 (its isoelectric point was 6.4)

TNF-98H: Polypeptide having an amino acid sequence of formula [I] in which 98th Pro was replaced by His TNF-103P: Polypeptide having an amino acid sequence of formula [I] in which 103rd Thr was replaced by Pro TNF-115T: Polypeptide having an amino acid sequence of formula [I] in which 115th Pro was replaced by Thr TNF-115H: Polypeptide having an amino acid sequence of formula [I] in which 115th Pro was replaced by His TNF-115R: Polypeptide having an amino acid sequence of formula [I] in which 115th Pro was replaced by Arg TNF-131I: Polypeptide having an amino acid sequence of formula [I] in which 131st Ser was replaced by Ile TNF-141Y: Polypeptide having an amino acid sequence of formula 8 I] in which 141st Asp was replaced by Tyr TNF-143V: Polypeptide having an amino acid sequence of formula [I] in which 143rd Ala was replaced by Val TNF-144K: Polypeptide having an amino acid sequence of formula [I] in which 144th Glu was replaced by Lys TNF-146E: Polypeptide having an amino acid sequence of formula [I] in which 146the Gly was replaced by Glu

EXAMPLE 10

Production of Other Human TNF Polypeptide Mutants-4

In accordance with example 1, expression plasmids for production of the following polypeptides were constructed. *Escherichia coli* was transformed with the expression plasmids. The transformants were cultured to produce the polypeptides.

TNF-32A: Polypeptide having an amino acid sequence of formula [I] in which 32nd Asn was replaced by Ala TNF-32C: Polypeptide having an amino acid sequence of formula [I] in which 32nd Asn was replaced by Cys TNF-32I: Polypeptide having an amino acid sequence of formula [I] in which 32nd Asn was replaced by Ile TNF-32R: Polypeptide having an amino acid sequence of formula [I] in which 32nd Asn was replaced by Arg TNF-32T: Polypeptide having an amino acid sequence of formula [I] in which 32nd Asn was replaced by Thr TNF-32V: Polypeptide having an amino acid sequence of formula [I] in which 32nd Asn was replaced by Val TNF-34I: Polypeptide having an amino acid sequence of formula [I] in which 34th Leu was replaced by Ile TNF-48M: Polypeptide having an amino acid sequence of formula [I] in which 48th Val was replaced by Met TNF-89I: Polypeptide having an amino acid sequence of formula [I] in which 89th Val was replaced by Ile TNF-94T: Polypeptide having an amino acid sequence of formula [I] in which 94th Ala was replaced by Thr TNF-97N: Polypeptide having an amino acid sequence of formula [I] in which 97th Ser was replaced by Asn TNF-98L: Polypeptide having an amino acid sequence of formula [I] in which 98th Pro was replaced by Leu TNF-113C: Polypeptide having an amino acid sequence of formula [I] in which 113th Tyr was replaced by Cys TNF-115Q: Polypeptide having an amino acid sequence of formula [I] in which 115th Pro was replaced by Gln TNF-115A: Polypeptide having an amino acid sequence of formula [I] in which 115th Pro was replaced by Ala TNF-115F: Polypeptide having an amino acid sequence of formula [I] in which 115th Pro was replaced by Phe TNF-115N: Polypeptide having an amino acid sequence of formula [I] in which 115th Pro was replaced by Asn TNF-115Y: Polypeptide having an amino acid sequence of formula [I] in which 115 th Pro was replaced by Tyr TNF-115V: Polypeptide having an amino acid sequence of formula [I] in which 115th Pro was replaced by Val TNF-115E: Polypeptide having an amino acid sequence of formula [I] in which 115th Pro was replaced by Glu TNF-115M: Polypeptide having an amino acid sequence of formula [I] in which 115th Pro was replaced by Met TNF-115I: Polypeptide having an amino acid sequence of formula [I] in which 115th Pro was replaced by Ile TNF-115W: Polypeptide having an amino acid sequence of formula [I] in which 115th Pro was replaced by Trp TNF-115K: Polypeptide having an amino acid sequence of formula [I] in which 115th Pro was replaced by Lys TNF-118Q: Polypeptide having an amino acid sequence of formula [I9 in which 118th Leu was replaced by Gln TNF-132T: Polypeptide having an amino acid sequence of formula [I] in which 132nd Ala was replaced by Thr TNF-145C: Polypeptide having an amino acid sequence of formula [I] in which 145th Ser was replaced by Cys TNF-153: POlypeptide having an amino acid sequence of formula [I] in which 153rd Ile was replaced by Leu

REFERENTIAL EXAMPLE 1

Construction of an Expression Plasmid for Producing Human

TNF

The cloned cDNA encoding human TNF was isolated by digestion with restriction endonuclease PstI, from the recombinant plasmid pHTNF13 prepared according to the method described in European Patent Publication No. 155549.

The cloned cDNA was digested with restriction endonuclease EcoRI to split off part of the non-coding region downstream of the TNF coding region. The resulting DNA fragment (about 1.1 kbp) was inserted into a larger DNA fragment prepared from a plasmid pBR322 by digestion with restriction endonucleases PstI and EcoRI to construct a recombinant plasmid including TNF cDNA and a tetracycline-resistance gene, which was named pHT113.

The recombinant plasmid pHT113 was digested with restriction endonucleases AvaI and SalI to cut it into three fragments (about 0.8 kbp, 1.3 kbp and 2.6 kbp in size). The 1.3 kbp-DNA fragment including most of the coding region for the human TNF and part of tetracycline-resistance gene was isolated (to be referred to as AvaI-SalI fragment). The AvaI-SalI fragment was ligated with the following chemically synthesized oligodeoxyribonucleotide adapter [f].

The resulting DNA fragment is referred to as HTNF-adapter fragment.

Separately, a DNA fragment (35 bp) including part of the trp promoter region was cut out from a plasmid pDR720 [P-L Biochemicals; D. R. Russell, et al., Gene, 20, 231 (1983)] by digestion with restriction endonucleases EcoRI and HpaI. The nucleotide sequence of the isolated 35 bp-DNA fragment is as follows:

The 35 bp-DNA fragment was ligated with a chemically synthesized adapter represented by the following formula:

5'-AACTAGTACGCAAGTTCACGTAAAAAGGGTAAT-3'   [g]
3'-TTGATCATGCGTTCAAGTGCATTTTTCCCATTAGC-5'

The resulting DNA fragment is referred to as trp promoter fragment.

A plasmid pBR322 was digested with restriction endonucleases EcoRI and SalI, and then the larger DNA fragment (about 3.7 kbp) was isolated.

Figure 9:
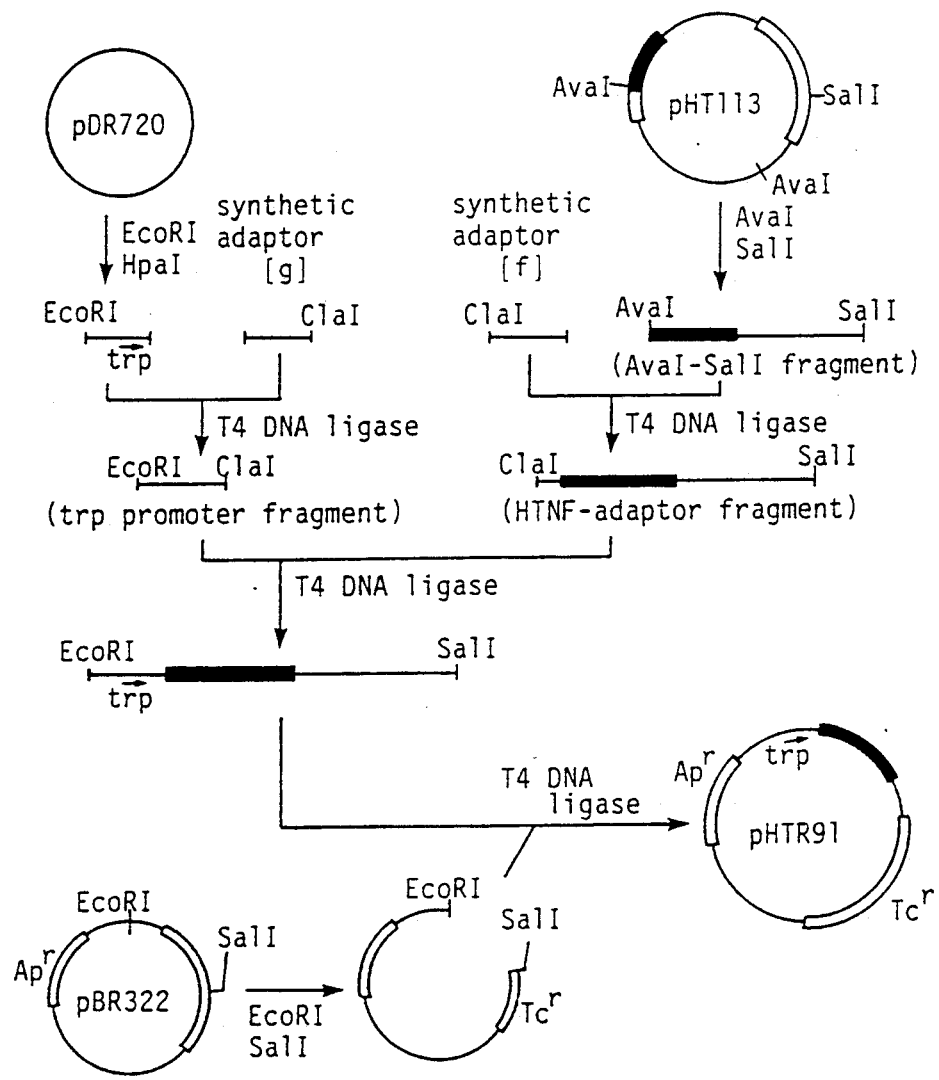
FIG. 9 shows the steps of constructing an expression plasmid pHTR91 (in Referential Example 1)

An expression plasmid for producing human TNF consisting of 155 amino acids corresponding to the amino acid sequence from amino acid No. 79 to No. 233 in Table 8, was constructed by sequential ligation of these three DNA fragments, the HTNF-adapter fragment, the trp promoter fragment and the larger pBR322 fragment (about 3.7 kbp) as illustrated in FIG. 9.

The expression plasmid was named pHTR91.

REFERENTIAL EXAMPLE 2

Construction of an Expression Plasmid for Producing a Modified Human TNF Polypeptide (147)

Figure 10:
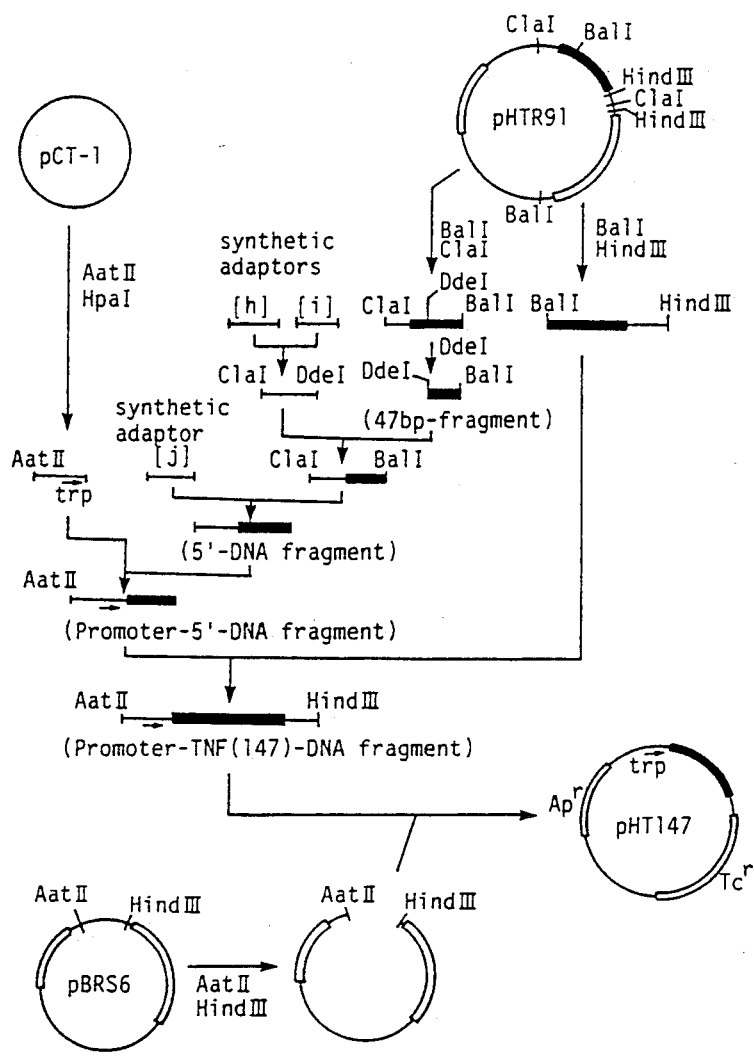
FIG. 10 shows the steps of constructing an expression plasmid pHT147 (in Referential Example 2)

An expression plasmid (pHT147) for producing a modified human TNF polypeptide consisting of 147 amino acids corresponding to amino acid No. 84 to No. 233 shown in Table 8, which is referred to as polypeptide TNF(147), was constructed as illustrated in FIG. 10.

The recombinant plasmid pHTR91 prepared as mentioned in Referential Example 1 was digested with restriction endonucleases ClaI and BalI to cut it into four DNA fragments. Two smaller DNA fragments (about 113 bp and 0.6 kbp in size) were isolated by 5% polyacrylamide gel electrophoresis. The smallest DNA fragment (113 bp) was further digested with restriction endonuclease DdeI to cut it into two fragment (47 bp and 66 bp), and the 47 bp-DNA fragment was isolated (to be referred to as 47 bp-fragment).

The 47 bp-fragment was ligated with two chemically synthesized adapters represented by the following formulae:

5'-CGATTATGAAGCCTGTAG-3'          [h]
    3'-TAATACTTCGGACATCGGG-5' and

5'-CCCATGTTGTAGCAAACCCTCAAGC-3'   [i]
    3'-TACAACATCGTTTGGGAGTTCGACT-5'

Furthermore, the resulting DNA fragment was ligated with the following chemically synthesized adapter [j].

[j]
5'-AACTAGTACGCAAGTTCACGTAAGGAGGTTAT-3'
3'-TTGATCATGCGTTCAAGTGCATTCCTCCAATAGC-5'

The ligated DNA fragment is referred to as 5'-DNA fragment.

Separately, a DNA fragment (about 380 bp in size) containing the trp promoter region was isolated from a plasmid pCT-1 [M. Ikehara et al., Proc. Natl. Acad. Sci. USA, 81, 5956 (1984)] by double digestion with restriction endonucleases HpaI and AatII.

The base sequence of the trp promoter region of the above 380 bp DNA fragment was reported by Bennett et al. [J. Mol. Biol., 121, 133 (1978)]. This DNA fragment was combined with the 5=-DNA fragment by using T4 DNA ligase.

The ligated DNA fragment is referred to as Promoter-5'-DNA fragment.

The DNA fragment (487 bp in size) containing a base sequence corresponding to the C-terminal region of human TNF polypeptide was cut out from the recombinant plasmid pHTR91 prepared as mentioned in Referential example 1, by double digestion with restriction endonucleases BalI and HindIII, and isolated.

This DNA fragment was ligated with the Promoter5'-DNA fragment by T4 DNA ligase. The ligated DNA fragment is referred to as Promoter-TNF(147)-DNA fragment.

Separately, the plasmid vector pBRS6 as shown in Example 1-(1) was cleaved with restriction endonucleases AatII and HindIII into two fragments. The larger DNA fragment (about 3.6 kbp) was isolated, and ligated by using T4 DNA ligase with the Promoter-TNF(147)-DNA fragment previously prepared in order to construct an expression plasmid pTH147 for producing the polypeptide TNF(147).

REFERENTIAL EXAMPLE 3

Figure 11:
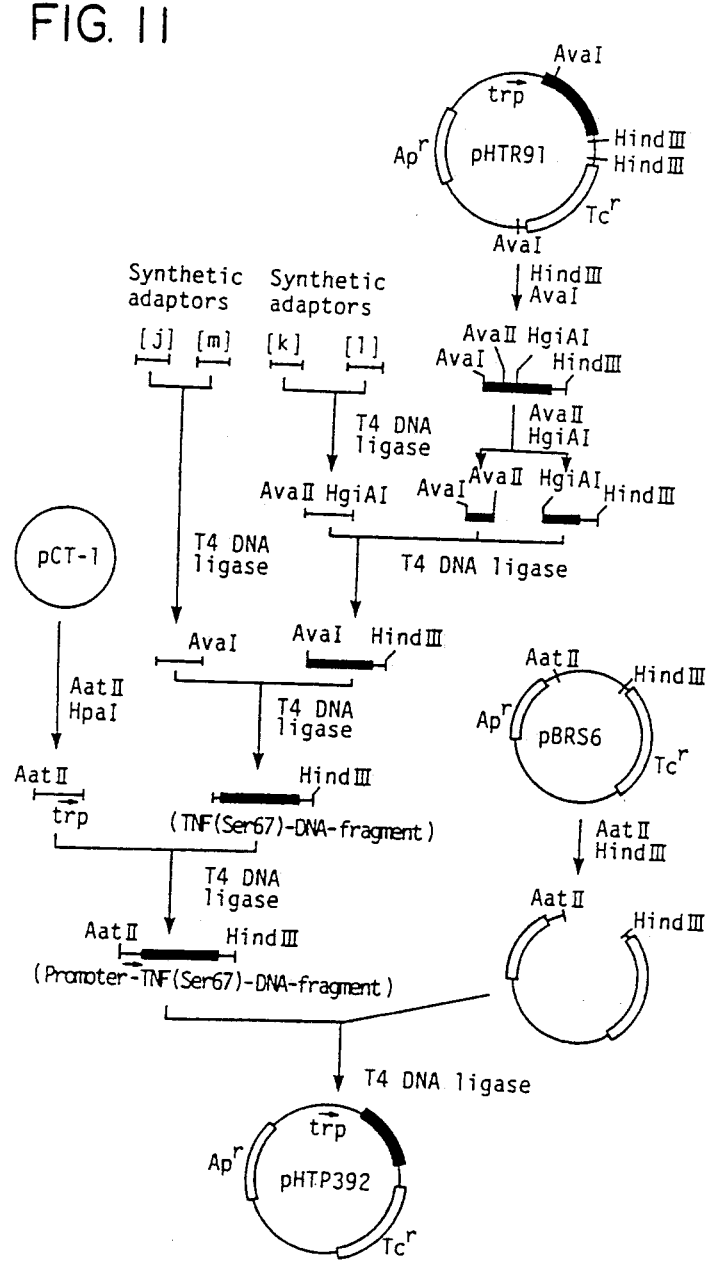
FIG. 11 shows the steps of constructing an on plasmid pHTP392 (in Referential Example 3).

Construction of an Expression Plasmid for Producing Human TNF Polypeptide Mutant TNF-67S An expression plasmid (pHTP392) for producing a polypeptide consisting of 155 amino acid and having an amino acid sequence corresponding to the sequence from amino acid No. 1 to No. 155 in Table 1, in which a cysteine residue in the 67th position from the N-terminus was replaced by a serine residue, referred to as TNF-67S, was constructed as illustrated in FIG. 11.

The recombinant plasmid pHTR91 prepared as mentioned in Referential Example 1 was digested with restriction endonucleases AvaI and HindIII to isolate about 600 bp DNA fragment corresponding to the base sequence of the downstream region from base No. 250 in Table 8. The 600 bp-DNA fragment was further digested with restriction endonucleases AvaII and HgiAI to cleave it into three DNA fragments (about 162 bp, 41 bp and 375 bp in size), and the 162 bp-DNA fragment and 375 bp-DNA fragment were isolated by polyacrylamide gel electrophoresis.

These DNA fragments were ligated with the following two chemically synthesized oligodeoxyribunucleotide adapters, [k] and [l], by using T4 DNA ligase.

5'-GTCCTCTTCAAGGGCCAA-3'          [k]
    3'-GAGAAGTTCCCGGTTCCGA-5' and

5'-GGCTC  TCCCTCCACCCATGTGCT-3'   [l]
    3'-GAGGGAGGTGGGTAC-5'

Furthermore, the resulting DNA fragment was sequentially ligated with the following two chemically synthesized oligodeoxyribonucleotide adapters, [j] and [m].

```
5'-AACTAGTACGCAAGTTCACGTAAGGAGGTAT-3'   [j]
3'-TTGATCATGCGTTCAAGTGCATTCCTCCAATAGC-5' and

5'-CGATTATGTCATCTTCTCGAACC-3'           [m]
3'-TAATACAGTAGAAGAGCTTGGGGCT-5'
```

The resulting DNA fragment is referred to as TNF(Ser67)-DNA fragment.

The DNA fragment (about 380 bp) containing the trp promoter region was isolated from a plasmid pCT-1 by double digestion with restriction endonucleases HpaI and AatII as shown in Referential Example 2.

This DNA fragment was combined with the TNF(Ser67)-DNA fragment by using T4 DNA ligase. The ligated DNA fragment is referred to as Promoter-TNF(Ser67)-DNA fragment.

Separately, the plasmid vector pBRS6 prepared as mentioned in Example 1-(1) was cleaved with restriction endonucleases AatII and HindIII into two fragments. The larger DNA fragment (about 3.6 kbp) was isolated, and ligated by T4 DNA ligase with the Promoter-TNF(Ser67)-DNA fragment previously prepared in order to construct expression plasmid pHTP392 for producing the TNF-67S.

In accordance with Example 1-(2), the plasmid was introduced into *Escherichia coli*. The transformant was cultured to produce TNF-67S.

REFERENTIAL EXAMPLE 4

Expression plasmids for production of the following polypeptides were constructed in accordance with Example 1-(1) and (2). The polypeptides were produced in *Escherichia coli* transformed with the expression plasmids.

TND-70Y: Polypeptide having an amino acid sequence of formula [I] in which 70th Thr was replaced by Tyr TNF-99S: Polypeptide having an amino acid sequence of formula [I] in which 99th Cys was replaced by Ser

REFERENTIAL EXAMPLE 5

In accordance with Example 1-(1) and (2), expression plasmids for production of the following polypeptides were constructed. Attempts were made to produce the polypeptides in *Escherichia coli* transformed with these expression plasmids. These polypeptides could not be extracted as soluble polypeptides or could be extracted only in small amounts.

TNF-12T: Polypeptide having an amino acid sequence of formula [I] in which 12th Ala was replaced by Thr TNF-13Y: Polypeptide having an amino acid sequence of formula [I] in which 13th His was replaced by Tyr TNF-14A: Polypeptide having an amino acid sequence of formula [I] in which 14th Val was replaced by Ala TNF-17T: Polypeptide having an amino acid sequence of formula [I] in which 17th Asn was replaced by Thr TNF-24F: Polypeptide having an amino acid sequence of formula [I] in which 24th Leu was replaced by Phe TNF-26R: Polypeptide having an amino acid sequence of formula [I] in which 26the Trp was replaced by Arg TNF-35P: POlypeptide having an amino acid sequence of formula [I] in which 35th Leu was replaced by Pro TNF-44D: Polypeptide having an amino acid sequence of formula [I] in which 44th Asn was replaced by Asp TNF-45P: Polypeptide having an amino acid sequence of formula [I] in which 45th Gln was replaced by Pro TNF-50P: Polypeptide having an amino acid sequence of formula [I] in which 50th Ser was replaced by Pro TNF-54C: Polypeptide having an amino acid sequence of formula [I] in which 54th Tyr was replaced by Cys TNF-54H: Polypeptide having an amino acid sequence of formula [I] in which 54th Tyr was replaced by His TNF-58P: Polypeptide having an amino acid sequence of formula [I] in which 58th Ser was replaced by Pro TNF-59L: Polypeptide having an amino acid sequence of formula [I] in which 59th Gln was replaced by Leu TNF-60D: Polypeptide having an amino acid sequence of formula [I] in which 60th Val was replaced by Asp TNF-60G: Polypeptide having an amino acid sequence of formula [I] in which 60th Val was replaced by Gly TNF-62S: Polypeptide having an amino acid sequence of formula [I] in which 62nd Phe was replaced by Ser TNF-93P: Polypeptide having an amino acid sequence of formula [I] in which 93rd Ser was replaced by Pro TNF-121G: POlypeptide having an amino acid sequence of formula [I] in which 121st Val was replaced by Gly TNF-124Q: POlypeptide having an amino acid sequence of formula [I] in which 124th Leu was replaced by Gln TNF-128A: Polypeptide having an amino acid sequence of formula [I] in which 128th Asp was replaced by Ala TNF-128N: Polypeptide having an amino acid sequence of formula [I] in which 128th Asp was replaced by Asn TNF-135D: Polypeptide having an amino acid sequence of formula [I] in which 135th Asn wa replaced by Asp TNF-138Y: Polypeptide having an amino acid sequence of formula [I] in which 138th Asp was replaced by Tyr TNF-148D: Polypeptide having an amino acid sequence of formula [I] in which 148th Val was replaced by Asp TNF-148G: Polypeptide having an amino acid sequence of formula [I] in which 148th Val was replaced by Gly TNF-150L: Polypeptide having an amino acid sequence of formula [I] in which 150th Phe was replaced by Leu TNF-151E: Polypeptide having an amino acid sequence of formula [I] in which 151th Gly was replaced by Glu

TABLE 8

```
                                    GACCCACGG
   -30         -20         -10         -1
    |           |           |           |
        CTCCACCCTCTCTCCCCTGGAAAGGACACC
    1           10          20          30
    |           |           |           |
    ATGAGCACTGAAAGCATGATCCGGGACGTG
    Met Ser Thr Glu Ser Met Ile Arg Asp Val
                                             |
                                             10
                40          50          60
                 |           |           |
    GAGCTGGCCGAGGAGGCGCTCCCCAAGAAG
    Glu Leu Ala Glu Glu Ala Leu Pro Lys Lys
                                             |
                                             20
```

TABLE 8-continued

```
          70          80          90
           |           |           |
    ACAGGGGGGCCCCAGGGCTCCAGGCGGTGC
    Thr Gly Gly Pro Gln Gly Ser Arg Arg Cys
                                          |
                                         30
         100         110         120
          |           |           |
    TTGTTCCTCAGCCTCTTCTCCTTCCTGATC
    Leu Phe Leu Ser Leu Phe Ser Phe Leu Ile
                                          |
                                         40
         130         140         150
          |           |           |
    GTGGCAGGCGCCACCACGCTCTTCTGCCTG
    Val Ala Gly Ala Thr Thr Leu Phe Cys Leu
                                          |
                                         50
         160         170         180
          |           |           |
    CTGCACTTTGGAGTGATCGGCCCCCAGAGG
    Leu His Phe Gly Val Ile Gly Pro Gln Arg
                                          |
                                         60
         190         200         210
          |           |           |
    GAAGAGTTCCCCAGGGACCTCTCTCTAATC
    Glu Glu Phe Pro Arg Asp Leu Ser Leu Ile
                                          |
                                         70
         220         230         240
          |           |           |
    AGCCCTCTGGCCCAGGCAGTCAGA(TCATCT
    Ser Pro Leu Ala Gln Ala Val Arg (Ser Ser
                                          |
                                         80
         250         260         270
          |           |           |
    TCTCGAACCCCGAGTGACAAGCCTGTAGCC
    Ser Arg Thr Pro Ser Asp Lys Pro Val Ala
                                          |
                                         90
         280         290         300
          |           |           |
    CATGTTGTAGCAAACCCTCAAGCTGAGGGG
    His Val Val Ala Asn Pro Gln Ala Glu Gly
                                          |
                                        100
         310         320         330
          |           |           |
    CAGCTCCAGTGGCTGAACCGCCGGGCCAAT
    Gln Leu Gln Trp Leu Asn Arg Arg Ala Asn
                                          |
                                        110
         340         350         360
          |           |           |
    GCCCTCCTGGCCAATGGCGTGGAGCTGAGA
    Ala Leu Leu Ala Asn Gly Val Glu Leu Arg
                                          |
                                        120
         370         380         390
          |           |           |
    GATAACCAGCTGGTGGTGCCATCAGAGGGC
    Asp Asn Gln Leu Val Val Pro Ser Glu Gly
                                          |
                                        130
         400         410         420
          |           |           |
    CTGTACCTCATCTACTCCCAGGTCCTCTTC
    Leu Try Leu Ile Tyr Ser Gln Val Leu Phe
                                          |
                                        140
         430         440         450
          |           |           |
    AAGGGCCAAGGCTGCCCCTCCACCCATGTG
    Lys Gly Gln Gly Cys Pro Ser Thr His Val
                                          |
                                        150
         460         470         480
          |           |           |
    CTCCTCACCCACACCATCAGCCGCATCGCC
    Leu Leu Thr His Thr Ile Ser Arg Ile Ala
                                          |
                                        160
```

TABLE 8-continued

```
         490         500         510
          |           |           |
    GTCTCCTACCAGACCAAGGTCAACCTCCTC
    Val Ser Tyr Gln Thr Lys Val Asn Leu Leu
                                          |
                                        170
         520         530         540
          |           |           |
    TCTGCCATCAAGAGCCCCTGCCAGAGGGAG
    Ser Ala Ile Lys Ser Pro Cys Gln Arg Glu
                                          |
                                        180
         550         560         570
          |           |           |
    ACCCCAGAGGGGGCTGAGGCCAAGCCCTGG
    Thr Pro Glu Gly Ala Glu Ala Lys Pro Trp
                                          |
                                        190
         580         590         600
          |           |           |
    TATGAGCCCATCTATCTGGGAGGGGTCTTC
    Tyr Glu Pro Ile Tyr Leu Gly Gly Val Phe
                                          |
                                        200
         610         620         630
          |           |           |
    CAGCTGGAGAAGGGTGACCGACTCAGCGCT
    Gln Leu Glu Lys Gly Asp Arg Leu Ser Ala
                                          |
                                        210
         640         650         660
          |           |           |
    GAGATCAATCGGCCCGACTATCTCGACTTT
    Glu Ile Asn Arg Pro Asp Tyr Leu Asp Phe
                                          |
                                        220
         670         680         690
          |           |           |
    GCCGAGTCTGGGCAGGTCTACTTTGGGATC
    Ala Glu Ser Gly Gln Val Tyr Phe Gly Ile
                                          |
                                        230
         700         710         720
          |           |           |
    ATTGCCCTG )TGAGGAGGACGAACATCCAAC
    Ile Ala Leu )
         730         740
          |           |
    CTTCCCAAACGCCTCCCCTGC
```

TABLE 9

```
     1          10          20          30
     |           |           |           |
    TCATCTTCTCGAACCCCGAGTGACAAGCCT
    Ser Ser Ser Arg Thr Pro Ser Asp Lys Pro
     |                                     |
     1                                    10

40          50          60
                 |           |           |
          GTAGCCCATGTTGTAGCAAACCCTCAAGCT
          Val Ala His Val Val Ala Asn Pro Gln Ala
                                                |
                                               20

70          80          90
                 |           |           |
          GAGGGGCAGCTCCAGTGGCTGAACCGCGG
          Glu Gly Gln Leu Gln Trp Leu Asn Arg Arg
                                                |
                                               30

100         110         120
                 |           |           |
          GCCTATGCCCTCCTGGCCAATGGCGTGGAG
          Ala Tyr Ala Leu Leu Ala Asn Gly Val Glu
                                                |
                                               40

130         140         150
                 |           |           |
          CTGAGAGATAACCAGCTGGTGGTGCCATCA
          Leu Arg Asp Asn Gln Leu Val Val Pro Ser
                                                |
                                               50
```

TABLE 9-continued

```
          160       170       180
           |         |         |
GAGGGCCTGTACCTCATCTACTCCCAGGTC
Glu Gly Leu Try Leu Ile Tyr Ser Gln Val
                                      |
                                     60

190       200       210
           |         |         |
CTCTTCAAGGGCCAAGGCTGCCCCTCCACC
Leu Phe Lys Gly Gln Gly Cys Pro Ser Thr
                                      |
                                     70

220       230       240
           |         |         |
CATGTGCTCCTCACCCACACCATCAGCCGC
His Val Leu Leu Thr His Thr Ile Ser Arg
                                      |
                                     80

250       260       270
           |         |         |
ATCGCCGTCTCCTACCAGACCAAGGTCAAC
Ile Ala Val Ser Tyr Gln Thr Lys Val Asn
                                      |
                                     90

280       290       300
           |         |         |
CTCCTCTCTGCCATCAAGAGCCCCTGCCAG
Leu Leu Ser Ala Ile Lys Ser Pro Cys Gln
                                      |
                                    100

310       320       330
           |         |         |
AGGGAGACCCCAGAGGGGGCTGAGGCCAAG
Arg Glu Thr Pro Glu Gly Ala Glu Ala Lys
                                      |
                                    110

340       350       360
           |         |         |
CCCTGGTATGAGCCCATCTATCTGGGAGGG
Pro Trp Tyr Glu Pro Ile Tyr Leu Gly Gly
                                      |
                                    120

370       380       390
           |         |         |
GTCTTCCAGCTGGAGAAGGGTGACCGACTC
Val Phe Gln Leu Glu Lys Gly Asp Arg Leu
                                      |
                                    130

400       410       420
           |         |         |
AGCGCTGAGATCAATCGGCCCGACTATCTC
Ser Ala Glu Ile Asn Arg Pro Asp Tyr Leu
                                      |
                                    140

430       440       450
           |         |         |
GACTTTGCCGAGTCTGGGCAGGTCTACTTT
Asp Phe Ala Glu Ser Gly Gln Val Tyr Phe
                                      |
                                    150

460
               |
        GGGATCATTGCCCTGTGA
        Gly Ile Ile Ala Leu ***
                        |
                       155
```

TABLE 10

```
   1       10        20        30
   |        |         |         |
TCATCTTCTCGAACCCCGAGTGACAAGCCT
Ser Ser Ser Arg Thr Pro Ser Asp Lys Pro
|                                     |
1                                    10
```

TABLE 10-continued

```
          40        50        60
           |         |         |
GTAGCCCATGTTGTAGCAAACCCTCAAGCT
Val Ala His Val Val Ala Asn Pro Gln Ala
                                      |
                                     20

70        80        90
           |         |         |
GAGGGGCAGCTCCAGTGGCTGAACCGCCGG
Glu Gly Gln Leu Gln Trp Leu Asn Arg Arg
                                      |
                                     30

100       110       120
           |         |         |
GCCTATGCCCTCCTGGCCAATGGCGTGGAG
Ala Tyr Ala Leu Leu Ala Asn Gly Val Glu
                                      |
                                     40

130       140       150
           |         |         |
CTGAGAGATAACCAGCTGGTGGTGCCATCA
Leu Arg Asp Asn Gln Leu Val Val Pro Ser
                                      |
                                     50

160       170       180
           |         |         |
GAGGGCCTGTACCTCATCTACTCCCAGGTC
Glu Gly Leu Try Leu Ile Tyr Ser Gln Val
                                      |
                                     60

190       200       210
           |         |         |
CTCTTCAAGGGCCAAGGCTGCCCCTCCACC
Leu Phe Lys Gly Gln Gly Cys Pro Ser Thr
                                      |
                                     70

220       230       240
           |         |         |
CATGTGCTCCTCACCCACACCATCAGCCGC
His Val Leu Leu Thr His Thr Ile Ser Arg
                                      |
                                     80

250       260       270
           |         |         |
ATCGCCGTCTCCTACCAGACCAAGGTCAAC
Ile Ala Val Ser Tyr Gln Thr Lys Val Asn
                                      |
                                     90

280       290       300
           |         |         |
CTCCTCTCTGCCATCAAGAGCCCCTGCCAG
Leu Leu Ser Ala Ile Lys Ser Pro Cys Gln
                                      |
                                    100

310       320       330
           |         |         |
AGGGAGACCCCAGAGGGGGCTGAGGCCAAG
Arg Glu Thr Pro Glu Gly Ala Glu Ala Lys
                                      |
                                    110

340       350       360
           |         |         |
CCCTGGTATGAGCTCATCTATCTGGGAGGG
Pro Trp Tyr Glu Leu Ile Tyr Leu Gly Gly
                                      |
                                    120

370       380       390
           |         |         |
GTCTTCCAGCTGGAGAAGGGTGACCGACTC
Val Phe Gln Leu Glu Lys Gly Asp Arg Leu
                                      |
                                    130
```

TABLE 10-continued

```
            400         410         420
             |           |           |
        AGCGCTGAGATCAATCGGCCCGACTATCTC
        Ser Ala Glu Ile Asn Arg Pro Asp Tyr Leu
                                             |
                                            140

430         440         450
             |           |           |
        GACTTTGCCGAGTCTGGGCAGGTCTACTTT
        Asp Phe Ala Glu Ser Gly Gln Val Tyr Phe
                                             |
                                            150

460
                         |
              GGGATCATTGCCCTGTGA
              Gly Ile Ile Ala Leu ***
                                |
                               155
```

What is claimed is:

1. A DNA having a base sequence represented by the following formula [A] in which 115th codon CCC is replaced by a codon CTC encoding Leu:

```
(5')  TCA TCT TCT CGA ACC CCG AGT GAC AAG 10
      CCT GTA GCC CAT GTT GTA GCA AAC CCT CAA 20
      GCT GAG GGG CAG CTC CAG TGG CTG AAC CGC 30
      CGG GCC AAT GCC CTC CTG GCC AAT GGC GTG 40
      GAG CTG AGA GAT AAC CAG CTG GTG GTG CCA 50
      TCA GAG GGC CTG TAC CTC ATC TAC TCC CAG 60
      GTC CTC TTC AAG GGC CAA GGC TGC CCC TCC 70
      ACC CAT CTG CTC CTC ACC CAC ACC ATC AGC 80
      CGC ATC GCC GTC TCC TAC CAG ACC AAG GTC 90
      AAC CTC CTC TCT GCC ATC AAG AGC CCC TGC 100
      CAG AGG GAG ACC CCA GAG GGG GCT GAG GCC 110
      AAG CCC TGG TAT GAG CCC ATC TAT CTG GGA 120
      GGG GTC TTC CAG CTG GAG AAG GGT GAC CGA 130
      CTC AGC GCT GAG ATC AAT CGG CCC GAC TAT 140
      CTC GAC TTT GCC GAG TCT GGG CAG GTC TAC 150
      TTT GGG ATC ATT GCC CTG-(3')     ...  [A]
```

2. A DNA having a base sequence encoding a polypeptide having an amino acid sequence represented by formula [I] in which the proline at position 115 is replaced by Leu, His, Ser, Gly, Thy or Asp:

| Ser | Ser | Ser | Arg | Thr | Pro | Ser | Asp | Lys | Pro |
|-----|-----|-----|-----|-----|-----|-----|-----|-----|-----|
| Val | Ala | His | Val | Val | Ala | Asn | Pro | Gln | Ala |
| Glu | Gly | Gln | Leu | Gln | Trp | Leu | Asn | Arg | Arg |
| Ala | Asn | Ala | Leu | Leu | Ala | Asn | Gly | Val | Glu |
| Leu | Arg | Asp | Asn | Gln | Leu | Val | Val | Pro | Ser |
| Glu | Gly | Leu | Tyr | Leu | Ile | Tyr | Ser | Gln | Val |
| Leu | Phe | Lys | Gly | Gln | Gly | Cys | Pro | Ser | Thr |
| His | Val | Leu | Leu | Thr | His | Thr | Ile | Ser | Arg |
| Ile | Ala | Val | Ser | Tyr | Gln | Thr | Lys | Val | Asn |
| Leu | Leu | Ser | Ala | Ile | Lys | Ser | Pro | Cys | Gln |
| Arg | Glu | Thr | Pro | Glu | Gly | Ala | Glu | Ala | Lys |
| Pro | Trp | Tyr | Glu | Pro | Ile | Tyr | Leu | Gly | Gly |
| Val | Phe | Gln | Leu | Glu | Lys | Gly | Asp | Arg | Leu |
| Ser | Ala | Glu | Ile | Asn | Arg | Pro | Asp | Tyr | Leu |
| Asp | Phe | Ala | Glu | Ser | Gly | Gln | Val | Tyr | Phe |
| Gly | Ile | Ile | Ala | Leu |     |     |     |     | [I].|

3. A DNA according to claim 2 wherein a translation initiation codon is joined to the 5'-terminus of the base sequence and/or a termination codon is joined to the 3'-terminus of the base sequence.

4. A vector having inserted thereinto a DNA according to claim 2.

5. A vector resulting from insertion of a DNA according to claim 2 into an expression vector.

6. A host cell transformed with the vector of claim 5.

7. The host cell according to claim 6 which is a microorganism.

8. The host cell according to claim 7 which is *Escherichia coli*.

9. A method for the production of a polypeptide encoded by a DNA as defined in claim 8 which comprises culturing a host cell transformed with a vector resulting from insertion of a DNA of claim 8 into an expression vector and isolating the resulting polypeptide encoded by the said DNA.

10. A DNA according to claim 1 wherein in the amino acid sequence of formula [I], the proline at position 115 is replaced by Leu.

* * * * *